United States Patent
Chen et al.

(10) Patent No.: US 11,126,390 B2
(45) Date of Patent: Sep. 21, 2021

(54) SYSTEM AND METHOD FOR CONTROLLING COORDINATION BETWEEN MEDICAL DEVICES, MEDICAL WORKSTATION AND COMMUNICATION DEVICE

(71) Applicant: SHENZHEN MINDRAY BIO-MEDICAL ELECTRONICS CO., LTD., Shenzhen (CN)

(72) Inventors: Dabing Chen, Shenzhen (CN); Jun Luo, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 31 days.

(21) Appl. No.: 16/026,882

(22) Filed: Jul. 3, 2018

(65) Prior Publication Data

US 2019/0026058 A1    Jan. 24, 2019

Related U.S. Application Data

(63) Continuation of application No. PCT/CN2016/070060, filed on Jan. 4, 2016.

(51) Int. Cl.
*G06F 3/14* (2006.01)
*A61B 5/00* (2006.01)
(Continued)

(52) U.S. Cl.
CPC .............. *G06F 3/1423* (2013.01); *A61B 5/00* (2013.01); *A61B 5/02141* (2013.01);
(Continued)

(58) Field of Classification Search
CPC ............... G09G 3/3614; G09G 3/3688; G09G 2310/0251; G09G 2310/0291;
(Continued)

(56) References Cited

U.S. PATENT DOCUMENTS

RE46,309 E * 2/2017 Go ........................ H04L 67/38
2002/0015106 A1   2/2002 Taylor, Jr.
(Continued)

FOREIGN PATENT DOCUMENTS

CN    102354186 A    2/2012
CN    103399584 A    11/2013
(Continued)

*Primary Examiner* — William Boddie
*Assistant Examiner* — Jeffrey Parker
(74) *Attorney, Agent, or Firm* — Kory D. Christensen

(57) ABSTRACT

A system and method for is disclosed for controlling coordination between medical devices, a medical workstation and a communication device. The system comprises: message transceiving units arranged corresponding to a plurality of medical detection display apparatuses respectively for forwarding, to a coordination message processing unit, interaction information acquired from an accessed external input device by the medical detection display apparatuses arranged corresponding to the message transceiving units themselves. The coordination message processing unit receives the interaction information from a message transceiving unit connected thereto, parses the interaction information to obtain an identifier corresponding to a medical detection display apparatus designated by a user, and converts the interaction information into a display message matching the designated medical detection display apparatus according to a display requirement corresponding to the identifier. By means of the present disclosure, the problem of the inconvenience in multi-screen operation control in the existing medical workstation is solved.

25 Claims, 14 Drawing Sheets

(51) Int. Cl.
  *H04L 29/02* (2006.01)
  *A61B 5/021* (2006.01)
  *A61B 6/00* (2006.01)
  *A61B 8/00* (2006.01)
  *A61M 16/01* (2006.01)
  *G09G 5/08* (2006.01)
  *G09G 5/12* (2006.01)

(52) U.S. Cl.
  CPC ............ *A61B 5/7425* (2013.01); *A61B 6/463* (2013.01); *A61B 8/463* (2013.01); *A61M 16/01* (2013.01); *G09G 5/08* (2013.01); *G09G 5/12* (2013.01); *H04L 29/02* (2013.01); *A61M 2205/3561* (2013.01); *A61M 2205/3584* (2013.01); *A61M 2205/502* (2013.01); *A61M 2205/505* (2013.01); *G09G 2354/00* (2013.01); *G09G 2370/022* (2013.01); *G09G 2370/24* (2013.01); *G09G 2380/08* (2013.01)

(58) Field of Classification Search
  CPC ....... G09G 2310/061; G09G 2300/026; G09G 2300/023; G06F 1/1541; G06F 1/1647; G06F 1/1649; G06F 1/1654; G06F 1/1683; G06F 3/1423; G06F 3/1431; G06F 3/1438; G06F 3/1446; G06F 3/1454; G06F 3/147
  See application file for complete search history.

(56) References Cited

U.S. PATENT DOCUMENTS

| 2008/0059598 A1* | 3/2008 | Garibaldi | G16H 40/63 |
| | | | 709/208 |
| 2012/0274558 A1 | 11/2012 | Broms et al. | |
| 2016/0055826 A1* | 2/2016 | Abe | G06F 3/1454 |
| | | | 345/2.3 |

FOREIGN PATENT DOCUMENTS

| CN | 103516887 A | 1/2014 |
| CN | 104415654 A | 3/2015 |
| CN | 104622500 A | 5/2015 |

* cited by examiner

SYSTEM AND METHOD FOR CONTROLLING COORDINATION BETWEEN MEDICAL DEVICES, MEDICAL WORKSTATION AND COMMUNICATION DEVICE

TECHNICAL FIELD

The present disclosure relates to medical devices, and more particularly to an interactive coordinated operation technology for a medical display workstation with multiple display screens.

BACKGROUND

An anesthesia workstation in an operating room usually requires a combination of a monitor, a personal computer (PC) connected to an information system, and an anesthesia machine. In clinical practice, when performing surgery for only one patient, the above three main types of medical detection display apparatuses all need to be controlled at the same time to share the patient's information. Conventional methods currently use external devices, such as a main controller, an interface switching unit, a switch, or similar hardware, and an external input device or an information sharing device is switched over among the various medical detection display apparatuses. In this way, the corresponding device sharing needs to be performed through hardware switching in the medical devices.

These conventional methods are costly and extremely inconvenient to use, and are not conducive to the sharing of the patient's information. For example, the monitor inputs the patient's information once, and at the same time, the anesthesia machine needs to perform device switching and inputs same again before it can obtain the corresponding input information.

These and other issues make conventional systems inconvenient and require further improvement.

SUMMARY

In one embodiment, a system is provided for controlling coordination between medical devices, for use between a plurality of medical detection display apparatuses. The system may include: a plurality of message transceiving units, one or more message communication channel being provided between the plurality of message transceiving units; and a coordination message processing unit connected to one of the plurality of message transceiving units, wherein the message transceiving units, which are respectively provided corresponding to the plurality of medical detection display apparatuses, are configured to acquire interaction information from an external input device accessing the medical detection display apparatuses and forward the interaction information to the coordination message processing unit.

In one embodiment, the coordination message processing unit is configured to receive the interaction information from the message transceiving unit connected thereto, parse the interaction information to obtain an identifier corresponding to a medical detection display apparatus specified by a user, and convert, according to a display requirement corresponding to the identifier, the interaction information into a corresponding display message for display on the specified medical detection display apparatus.

The message transceiving unit may be connected to the coordination message processing unit which may be configured to acquire, based on the identifier, information about a transmission path of the specified medical detection display apparatus in the message communication channel, and transmit a transmission message carrying the display message and the transmission path information to the message transceiving unit provided corresponding to the specified medical detection display apparatus via the message communication channel, such that the message transceiving unit receives the transmission message, and the display message is output and displayed on the specified medical detection display apparatus.

In one embodiment, a medical workstation may include: a plurality of medical detection display apparatus; an external input device connected to one of the plurality of medical detection display apparatuses; and a system for controlling coordination between medical devices as described above, the system including a plurality of message transceiving units and a coordination message processing unit, wherein the plurality of medical detection display apparatuses are connected to each other to form a message communication channel between the plurality of message transceiving units. Each of the medical detection display apparatuses may be provided with the corresponding message transceiving unit.

In one embodiment, a method for controlling coordination between medical devices, for use between a plurality of medical detection display apparatuses having a message communication channel, may include: acquiring interaction information from an external input device accessing one of the plurality of medical detection display apparatuses and forwarding same; receiving the interaction information and parsing the interaction information to obtain a medical detection display apparatus specified by a user; converting the interaction information into a display message matching the display requirements corresponding to the specified medical detection display apparatus; acquiring information about a transmission path of the specified medical detection display apparatus in the message communication channel; transmitting a transmission message carrying the presentation message and the transmission path information to the specified medical detection display apparatus via the message communication channel; and receiving the transmission message and outputting and displaying the display message on the specified medical detection display apparatus.

In one embodiment, a communication device for accessing a message communication channel formed by a plurality of medical detection display apparatuses may include: a storage unit configured to pre-store correspondence relationships between identifiers corresponding to the plurality of medical detection display apparatuses, and information about transmission paths of the plurality of medical detection display apparatuses in the message communication channel and corresponding display requirements; a communication unit configured to receive external interaction information acquired from an external input device accessing one of the plurality of medical detection display apparatuses; and a processing unit configured to parse the interaction information to obtain an identifier corresponding to a medical detection display apparatus specified by a user, and convert the interaction information into a display message matching the specified medical detection display apparatus according to a display requirement. The communication unit may be further configured to obtain, according to the identifier, information about a transmission path of the specified medical detection display apparatus in the message communication channel, and transmit a transmission message carrying the display message and the transmission path information to the specified medical detection display apparatus via the message communication channel.

DETAILED DESCRIPTION

In conventional medical workstations, where multiple types of medical detection display apparatuses all work independently, there is an inconvenient factor that requires one-by-one operation control if the medical detection display apparatuses are controlled by an external input device. The present disclosure can use one access of the external input device to control display operation areas of all the medical detection display apparatuses by means of the device interconnection technology and the message transmission mechanism disclosed herein.

Figure 1:
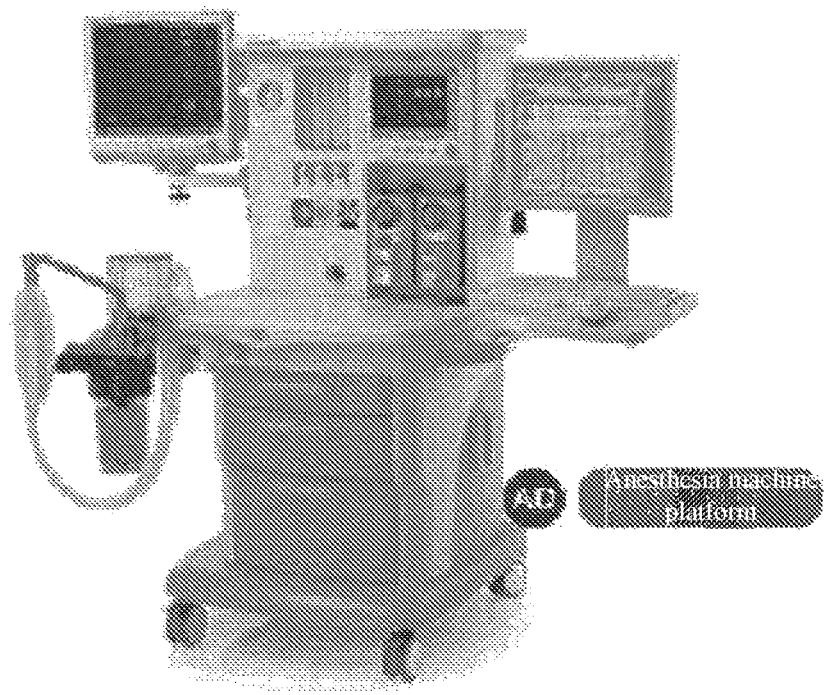
FIG. 1 is a schematic structural diagram of an anesthesia workstation in one embodiment of the present disclosure.

FIG. 1 illustrates a mobile medical workstation, which comprises a monitor, an anesthesia machine, and a PC (information system) machine. Herein, devices having separate displays, such as the monitor, the anesthesia machine, the PC, an ultrasonic detector, a CT scanner, a blood pressure detector, a blood collector, and the X-ray machine, are collectively referred to as "medical detection display apparatuses. In general, all three medical detection display apparatuses illustrated in FIG. 1 need to be operable at the same time and need to be independently controlled by using an external input device (or a control device). The conventional external input device (i.e., human-machine interaction control device) may include at least one of a mouse, a keyboard, a barcode, a remote controller, a mobile phone with a control or remote operation, a scroll wheel, etc. The information sharing device may at least include one of a U disk, a hard disk, an SD card, and other devices for directly storing information, and may further comprise a network card, a Bluetooth device, etc. It is possible to obtain shared information from other devices or a cloud database via the network card, the Bluetooth device, etc. The shared information herein may include any kind of data that may be displayed on the display, or a set of instructions that can display the progress on the display after running, or the like.

The three medical detection display apparatuses may be connected through a wired network or a wireless network, or through an ordinary serial port, or by means of any other method, to form a message communication channel. Of course, the embodiments of the present disclosure are not limited to a medical workstation having three medical detection display apparatuses, but can also be applied to a medical workstation including two or more medical detection display apparatuses. After the technique disclosed in the present disclosure is used between a plurality of medical detection display apparatuses, when the mouse is moved to a screen of the monitor, messages input by the keyboards, mice, etc. corresponding to all the medical detection display apparatus are directly displayed on the monitor; when the mouse is moved to the anesthesia machine, the input from the external device such as the keyboard is only valid on the anesthesia machine; when the mouse is moved to the PC machine, the input from the external device such as the keyboard is only valid on the PC, etc.

The external input device accessing any one of the plurality of medical detection display apparatuses may be used to operate and control any one of the plurality of medical detection display apparatuses. For example, the external input device on any one of the medical detection display apparatuses may be used to perform interactive operations, such as inputting text information, controlling the cursor movement, and inputting control commands, on any one of the medical detection display apparatuses. Herein, the plurality of medical detection display apparatuses includes two or more medical detection display apparatuses. In addition, the plurality of medical detection display apparatuses herein may be apparatuses that come from different manufacturers, are of different models, and realize different detection functions, and the control of coordination between the plurality of medical detection display apparatuses may be accomplished without modifying/changing the hardware of the device itself, thereby saving costs, facilitating user operation, and improving the user experience.

Figure 2:
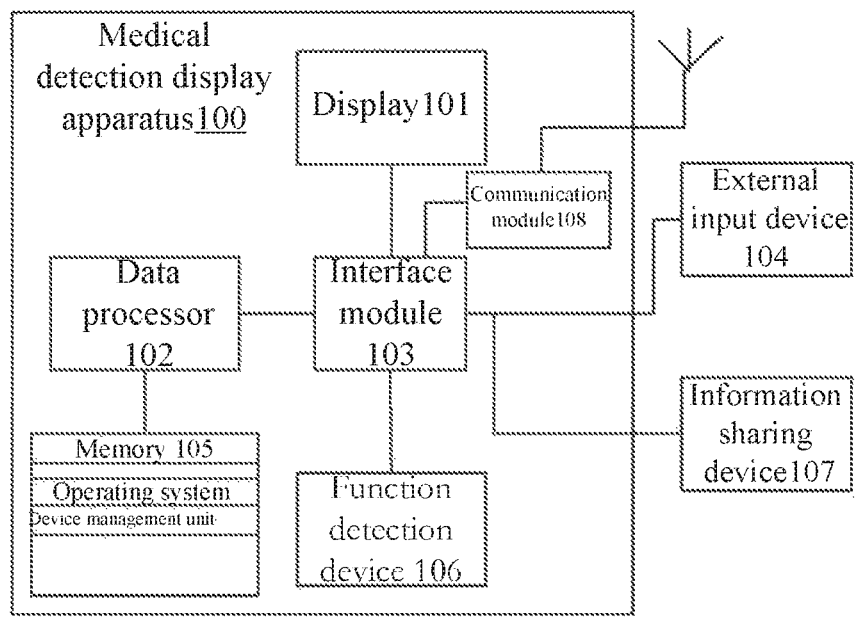
FIG. 2 is a schematic structural diagram of a medical detection display apparatus in one embodiment of the present disclosure.

FIG. 2 is a hardware architecture diagram of the medical detection display apparatus described above. For each medical detection display apparatus, whether it is the monitor, the anesthesia machine, the PC information system machine, the X-ray machine, or the like, it can comprise a display 101, a processor 102, a memory 105, and an interface unit 103. The external input device 104, the information sharing device 107, and the display 101 are respectively connected to the processor 102 via the interface unit 103. The processor 102 is connected to the memory 105. A software system unit located over a hardware layer is recorded on the memory 105, which software system unit includes an operating system and a device management unit of a hardware device connected to the medical detection display apparatus via the interface unit 103, for example, a drive unit including the external input device 104 such as the mouse and the keyboard, and/or the information sharing device 107 connected to the medical detection display apparatus via the interface unit 103, and a drive unit further including a display device.

The display 101 is configured to display visual information presented on a display interface. The processor 102 is connected to the external input device 104 and/or the information sharing device 107 via the interface unit 103, acquiring interaction information and/or shared information from the external input device 104 and/or the information sharing device 107, and transferring same, after being analyzed, to the display 101 for display. In addition, the interface unit 103 may also comprise or be connected to a communication unit 108. The communication unit 108 may use a wireless or wired network standard, such as Wi-Fi, GSM, CDMA, 3G, and LAN. The communication unit 108 may be connected to the processor 102 via the interface unit 103 for obtaining information from an external wireless network or a wired network. Here, the wireless network or the wired network is the message communication channel mentioned herein. Of course, the medical detection display apparatus may also be directly connected to the other medical detection display apparatuses via the hardware provided in the interface unit 103, such as a serial port, a network interface, and a USB interface, in order to obtain the message communication channel.

The processor 102 here may be one or more processors or controllers. The memory 105 may also be a memory chip or a memory chipset. In addition, for the medical detection display apparatus 100 having or connected to a function detection device 106, the function detection device 106 is also connected to the processor 102 via the interface unit 103, so that the processor 102 obtains the detection data from the function detection device 106, and displays the same, after being analyzed, on the display 101. The functional detection device 106 herein may be an X-ray image acquisition device in the X-ray machine, a monitoring component in the monitor, an ultrasound probe on an ultrasound monitor, etc. The interface unit 103 may be one or more separately provided interfaces, and the various external devices, sharing devices, and the like, are connected to the processor 102 via the interface unit, or the external devices and sharing devices are respectively connected to the processor 102 via the respective interfaces.

Figure 4A:
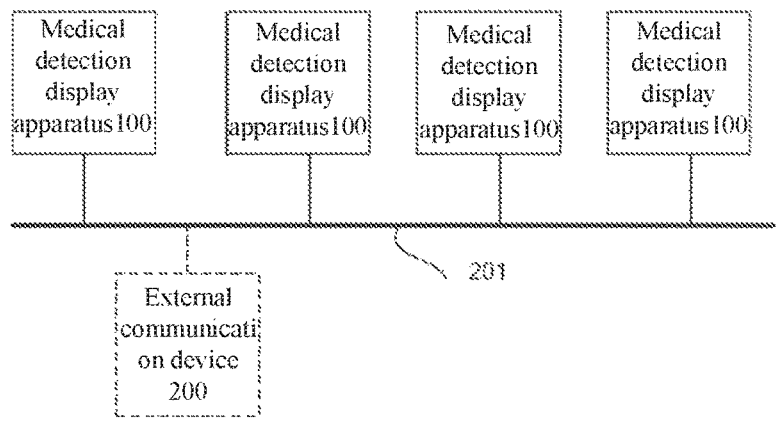
FIGS. 4A, 4B and 4C are schematic diagrams of connection relationships between a plurality of medical detection display apparatuses in various embodiments of the present disclosure.
Figure 4B:
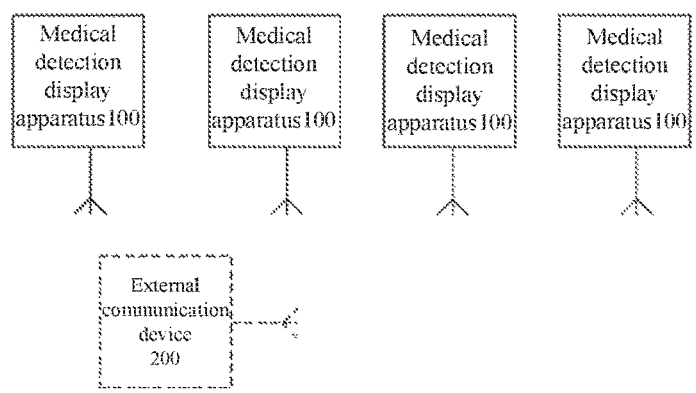
Figure 4C:
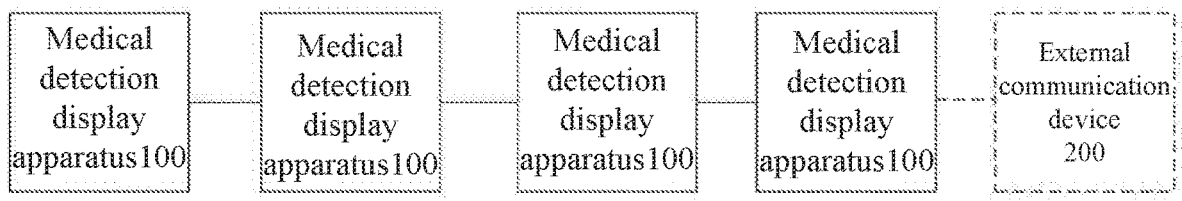

In one embodiment of the present disclosure, a plurality of medical detection display apparatuses shown in FIG. 1 may implement the message communication channel between the plurality of medical detection display apparatuses using multiple methods shown in FIGS. 4A to 4C (the content indicated by the dashed line box in FIG. 4 may or may not appear at the same time as the contents indicated by the solid line boxes).

Initially, as shown in FIG. 4A, the plurality of medical detection display apparatuses shown in FIG. 1 may be connected via a wired network 201 to obtain the message communication channel for transferring the message. The wired network may be a local area network connected via a bus or a local area network connected via a wired network line.

Moreover, as shown in FIG. 4B, the plurality of medical detection display apparatuses shown in FIG. 1 may be connected via a wireless network to obtain the message communication channel for transferring the message. The wireless network may be a wireless network implemented by means of Bluetooth, Wi-Fi, GSM, CDMA, 3G, etc.

In addition, as shown in FIG. 4C, a plurality of medical detection display apparatuses shown in FIG. 1 may also be connected in series via hardware interfaces, such as serial interfaces, network interfaces, and USB interfaces, to form the message communication channel for transferring the message.

Furthermore, on the basis of the architecture represented by the solid line in FIG. 4A, a communication device 200 separated from the plurality of medical detection display apparatuses is added in the dashed line box, and the plurality of medical detection display apparatuses shown in FIG. 1 are also connected to the communication device 200 via the wired network 201.

Additionally, on the basis of the architecture represented by the solid line in FIG. 4B, a communication device 200 is added in the dashed line box, and the plurality of medical detection display apparatuses shown in FIG. 1 are also connected to the communication device 200 via the wireless network 201.

Finally, on the basis of the architecture represented by the solid line in FIG. 4C, a communication device 200 is added in the dashed line box, and the plurality of medical detection display apparatuses shown in FIG. 1 are also connected in series to the communication device 200 via the hardware interfaces. The communication device 200 may be located between the plurality of medical detection display apparatuses 100, or may be located at the head or tail end of the message communication channel formed by the plurality of medical detection display apparatuses 100.

Figure 3:
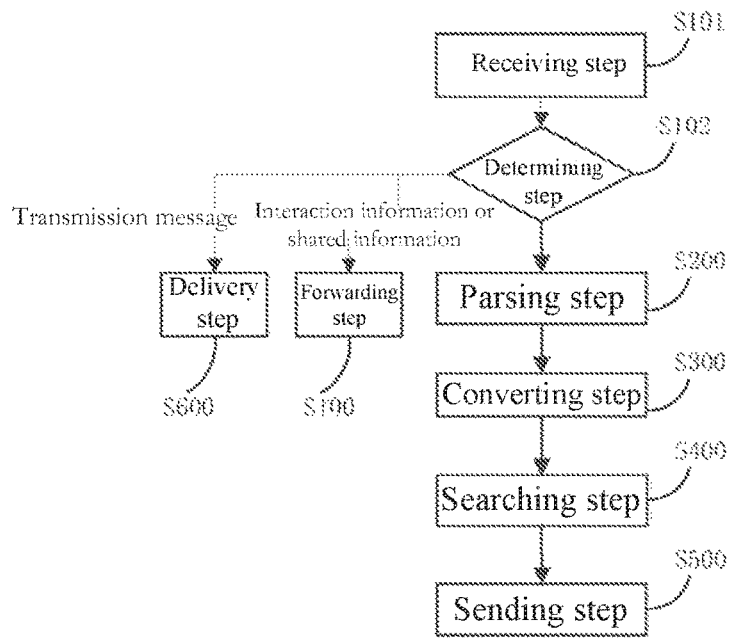
FIG. 3 is a schematic flowchart of a method in one embodiment of the present disclosure.

Based on the multiple connection methods for forming the above message communication channel, FIG. 3 provides a method for controlling coordination between medical devices, which may be applied to the above various connection methods. In order to facilitate the transferring of the message, in one embodiment of the present disclosure, a central machine may be first provided in the above message communication channel, and the message in the message communication channel is uniformly processed and parsed by the central machine, and is then sent to the other devices in the message communication channel, for example, the central machine may be used to perform a parsing step S200, a converting step S300, a sending step S500, and a searching step S400 of the method illustrated in FIG. 3. Of course, when the central machine needs to obtain interaction information or shared information from an external input device or an information sharing device connected to its own device, the central unit may also execute a receiving step S101. This central machine may be selected from the plurality of medical detection display apparatuses, or the above-described communication device 200 may be use as the central machine. Regardless of who the central machine belongs to, the implementation of a method for controlling coordination between medical devices provided in FIG. 3 would not be affected.

In order to facilitate the transmission of the message in the message communication channel, transmission path information corresponding to each device located on the message communication channel may be stored on the storage device in advance, or a configuration result of the transmission path information of each device located on the message communication channel may be recorded when the coordinated operation method of the present disclosure is initiated. Based on the different mechanisms for forming the message communication channel, the contents included in the transmission path information will be different.

As an example, a corresponding network communication address of each of the medical detection display apparatuses and/or the communication device in the network may be the above-mentioned transmission path information when the message communication channel is formed by means of the wireless or wired network. As another example, information about a communication path between each of the medical detection display apparatuses and the central machine may be the above-described transmission path information when the message communication channel is formed by means of the serial connection via the hardware interfaces. The information about a communication path between each of the medical detection display apparatuses and the central machine includes information about a communication path from a certain medical detection display apparatus to the central machine, and information about a communication path from the central machine to the certain medical detection display apparatus.

As shown in FIG. 4C, on the message communication channel formed by means of the serial connection via the hardware interfaces, if it is assumed that the third medical detection display apparatus 100 from left to right is the central machine, the communication path from the left first medical detection display apparatus 100 to the central machine is from the left first medical detection display apparatus 100, through the left second medical detection display apparatus 100, to the third medical detection display apparatus 100 in sequence, and vice versa. If it is assumed that the communication device 200 is the central machine, the communication path from the left first medical detection display apparatus 100 to the central machine is from the left first medical detection display apparatus 100, through the left second medical detection display apparatus 100, the third medical detection display apparatus 100 and the fourth medical detection display apparatus 100 to the communication device 200 in sequence, and vice versa. It may be seen that the message is forwarded multiple times or passes through the plurality of medical detection display apparatuses on the communication path. Therefore, based on the hardware system architecture shown in FIG. 4C, the communication path information mentioned herein may include one of the following:

1. A sequence of all the medical detection display apparatus and/or the communication device that have passed during the process of reaching a target node, wherein the target node is an object to which the message was finally transmitted, and may comprise: the medical detection display apparatus specified by a user through the external input device, or the central machine. As an example, if it is assumed that the communication device 200 is the central machine, the information about the communication path from the left first medical detection display apparatus 100 to the central machine may be the execution sequence from the left first medical detection display apparatus 100, through the left second medical detection display apparatus 100, the third medical detection display apparatus 100 and the fourth medical detection display apparatus 100, to the communication device 200.

2. Corresponding numbers of all the medical detection display apparatus and/or the communication device that have passed during the process of reaching the target node in the communication path information. If it is assumed that the third medical detection display apparatus 100 from left to right is the central machine, starting from the left, the first medical detection display apparatus 100, the left second medical detection display apparatus 100, the third medical detection display apparatus 100, and the fourth medical detection display apparatus 100 are sequentially numbered 1, 2, 3 and 4, and 3 represents the central machine, the information about the communication path from the central machine to the left first medical detection display apparatus 100 may be "2, 1".

3. A corresponding number of the target node in the communication path information. Referring to the example of Point 2, the information about the communication path from the central machine to the left first medical detection display apparatus 100 may be "1".

4. The number of times of forwarding required to reach the target node. Referring to the example of Point 1, from the left first medical detection display apparatus 100 to the central machine, multiple times of forwarding need to be performed by means of adjacent medical detection display apparatuses, for example, the second medical detection display apparatus 100, the third medical detection display apparatus 100 and the fourth medical detection display apparatus 100 respectively need to forward the message once, so that the communication path information includes: the number of times of forwarding is 4.

5. A corresponding number of the target node and the number of times of forwarding required to reach the target node. Referring to the example of Point 2, the information about the communication path from the central machine to the left first medical detection display apparatus 100 may be "1", and the number of times of forwarding is 2.

By means of the above-mentioned communication path information, it may be determined whether the message forwarded on the message communication channel is sent to itself, which will be described in detail below. The corresponding numbers of the medical detection display apparatuses and/or the communication device in the communication path information as mentioned above are distinguishing marks used by a computer to distinguish between the plurality of medical detection display apparatuses and/or the communication device, and may be sequential numbers, marks, and device production labels, and any one of the distinguishing marks in the coordinate position and the like corresponding to the display installation position relationship map as mentioned below.

Based on the above-mentioned various mechanisms of forming the message communication channel, various specific embodiments of the present disclosure will be described in detail below with reference to the accompanying drawings. Referring to FIG. 3, a flowchart of a method is shown for controlling coordination between medical devices.

In the receiving step S101, interaction information is received, which is acquired from an external input device accessing one of a plurality of medical detection display apparatuses.

The external input device may access one of the plurality of medical detection display apparatuses by connecting an interface unit 103. The medical detection display apparatus actually connected to the external input device acquires the interaction information from the external input device. The interaction information herein is user instructions input by the user via the external input device, including the mouse double-click, the movement of the mouse, text input, graphic input and other interaction information, i.e., the interaction information may comprise cursor movement information for controlling the movement of the cursor, and input icon information and instruction information.

Of course, in this embodiment, the external input device may access one of the plurality of medical detection display apparatuses for controlling the plurality of medical detection display apparatuses. Alternatively, a plurality of external input devices respectively access the plurality of medical detection display apparatuses, any one of the external detection devices may also be used to control any one of the plurality of medical detection display apparatuses.

In one embodiment of the present disclosure, the receiving step S101 further includes receiving shared information acquired from an information sharing device accessing one of the plurality of medical detection display apparatuses.

Figure 21:
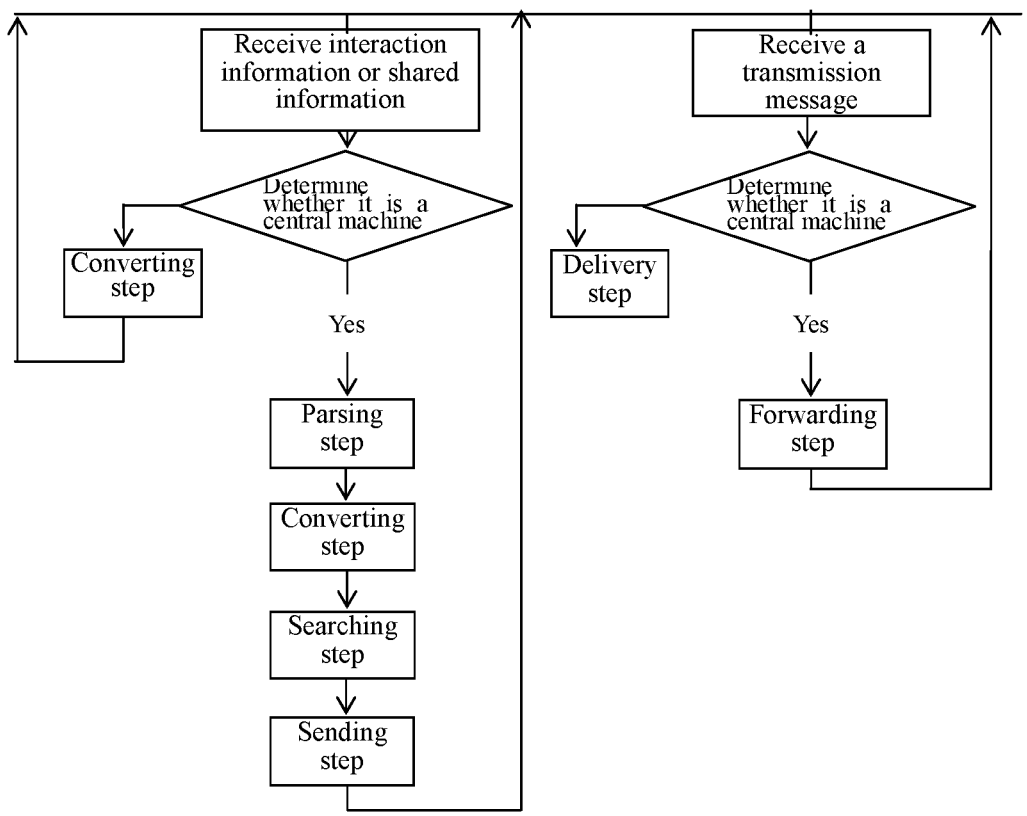
FIG. 21 is a schematic flowchart of a method in an embodiment.

The device, which receives the interaction information or the shared information, may or may not be the central machine in the message communication channel, and would perform different processing for the different identities in the message communication channel. Therefore, in one embodiment of the present disclosure, as shown in FIG. 21, the following determining step S102 is further comprised before the parsing step S200:

determining whether the device, which receives the message, is a central machine in the message communication channel, the central machine being one of the plurality of medical detection display apparatuses of the communication device independent of the plurality of medical detection display apparatuses; if so, respectively performing the parsing step, the converting step, the searching step, and the sending step on the received interaction information or shared information; otherwise, if the received message is the interaction information or the shared information, performing a forwarding step S100: forwarding the received interaction information or shared information to the central machine; and if the received message is a transmission message, performing a delivery step S600: outputting and displaying a display message or a presentation message on the specified medical detection display apparatus.

The different methods for forwarding the interaction information or the shared information in this embodiment are used according to the mechanisms for forming the message communication channel between the plurality of medical detection display apparatuses.

As an example, in the message communication channel shown in FIG. 4A or 4B, the interaction information or shared information, after the network communication address of the central machine in the network is embedded therein, is sent to the network to forward the interaction information or the shared information to the central machine.

As another example, in the message communication channel shown in FIG. 4C, the interaction information or shared information, after the information about the communication path from the medical detection display apparatus accessing the external input device or the information sharing device to the central machine is embedded therein, is forwarded to an adjacent medical detection display apparatus located on the message communication channel to forward the interaction information or shared information to the central machine.

The above-mentioned central machine may be one of the plurality of medical detection display apparatuses, or the communication device.

In one embodiment of the present disclosure, the forwarding step further includes:

determining whether the device, which acquires the interaction information or shared information is a central machine itself; if so, the device executing the parsing step, the converting step, the searching step, and the sending step; otherwise, forwarding the acquired interaction information or shared information to the message communication channel. The mode of forwarding to the message communication channel may be sending to the network or sending to the target node depending on the information about the communication path from the device to the central machine.

In the parsing step S200, the above interaction information is parsed to obtain a medical detection display apparatus specified by a user.

The interaction information in this embodiment may comprise at least an interaction information for controlling the movement of the cursor, referred to herein as cursor movement information. This cursor movement information includes at least one of: a cursor movement speed, a cursor movement displacement, a cursor movement direction, etc. The cursor movement in this embodiment may be controlled by any external input device, such as a mouse, a scroll wheel, or a keyboard, which will not be enumerated here.

Figure 5:
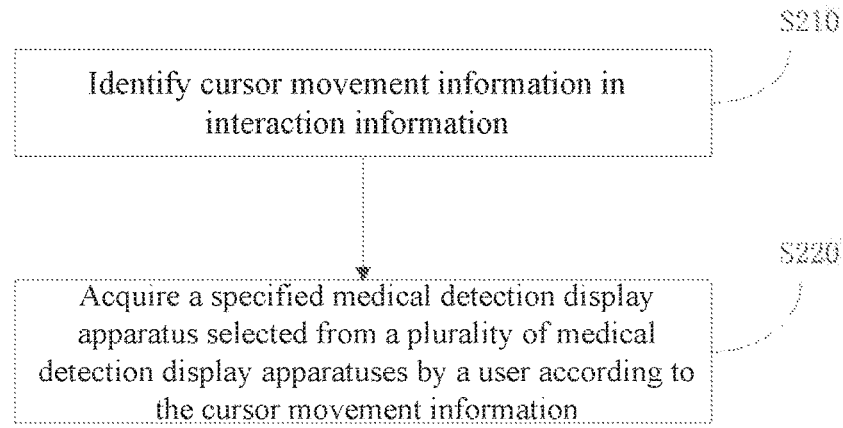
FIG. 5 is a schematic flowchart of a method in one embodiment of the present disclosure.

With the cursor movement information, it is possible to easily determine which medical detection display apparatus the user has specified. As an example, in one embodiment of the present disclosure, as shown in FIG. 5, the above step S200 includes:

Step S210 of identifying the cursor movement information in the interaction information, in which the cursor movement information may be determined by identifying an input operation performed when any external input device, such as a mouse, a scroll wheel, or a keyboard controls the cursor in the interface; and Step S220 of acquiring the specified medical detection display apparatus selected from the plurality of medical detection display apparatuses by the user according to the cursor movement information.

Of course, other methods may also be used in this embodiment, for example, the user's specification is determined by identifying the movement of the user's gesture, or by identifying which medical detection display apparatus the external input device is located in, and so on. For example, the device is provided with a sensor for sensing the actual position of the mouse to determine which medical detection display apparatus the mouse is located in. Specifically, the sensor may be installed on the display device, and when the mouse appears within the sensing or effective range of the display device sensor, the mouse is identified as controlling the display device, and so on, which will not be enumerated here. In the following, various specific embodiments of the present disclosure will be described in detail by taking the use of the cursor movement information as an example.

As an example, in one embodiment of the present disclosure, in the above step S220, according to pre-stored display installation position relationships of the plurality of medical detection display apparatuses and based on the cursor movement information, the correspondence relationship between the motion of a cursor and the display installation position relationship is determined, so as to determine the specified medical detection display apparatus selected by the user from the plurality of medical detection display apparatuses.

Figure 6:
FIG. 6 is a schematic diagram of a spatial position relationship of three displays in one embodiment of the present disclosure.
Figure 6:
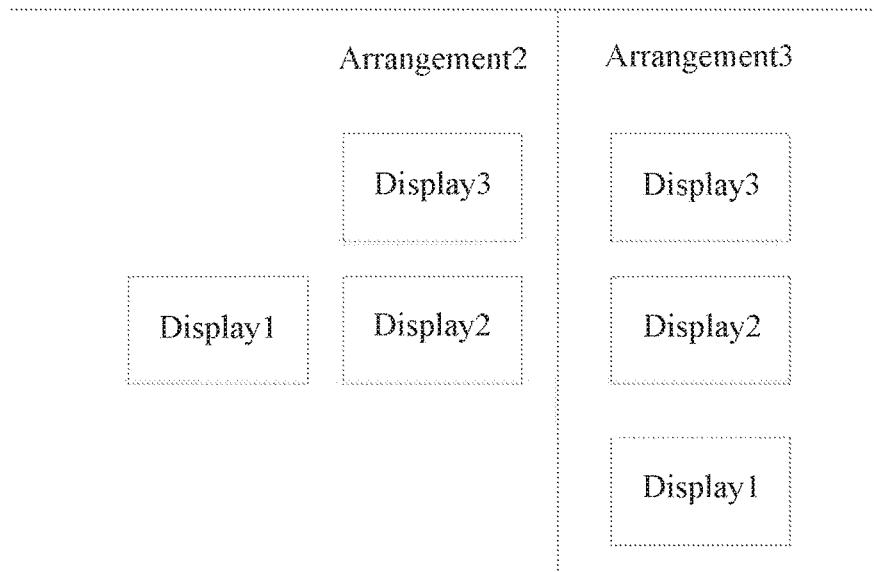

The display installation position relationships of the plurality of medical detection display apparatuses mentioned herein are the spatial placement relationships of displays in the plurality of medical detection display apparatus. Taking the medical workstation shown in FIG. 1 as an example, the workstation has three displays, and there may be at least three arrangements as shown in FIG. 6. In order to facilitate the machine identification and reference, the display installation position relationships may be saved by using a coordinate map. The cursor movement information includes information, such as the movement speed of the cursor, the movement direction of the cursor, the movement displacement of the cursor, and the movement range of the cursor. The motion of the cursor obtained based on the cursor movement information refers to the motion result or the motion process, for example, the cursor moves in a particular direction, the final position after the cursor is moved, etc.

The motion of the cursor includes the movement speed, movement direction, movement displacement, movement range and other information of the cursor. By using the display installation position relationships, the control of the motion of the cursor movement by the external input device may be combined to specify and confirm the medical detection display apparatus in various ways.

Figure 7:
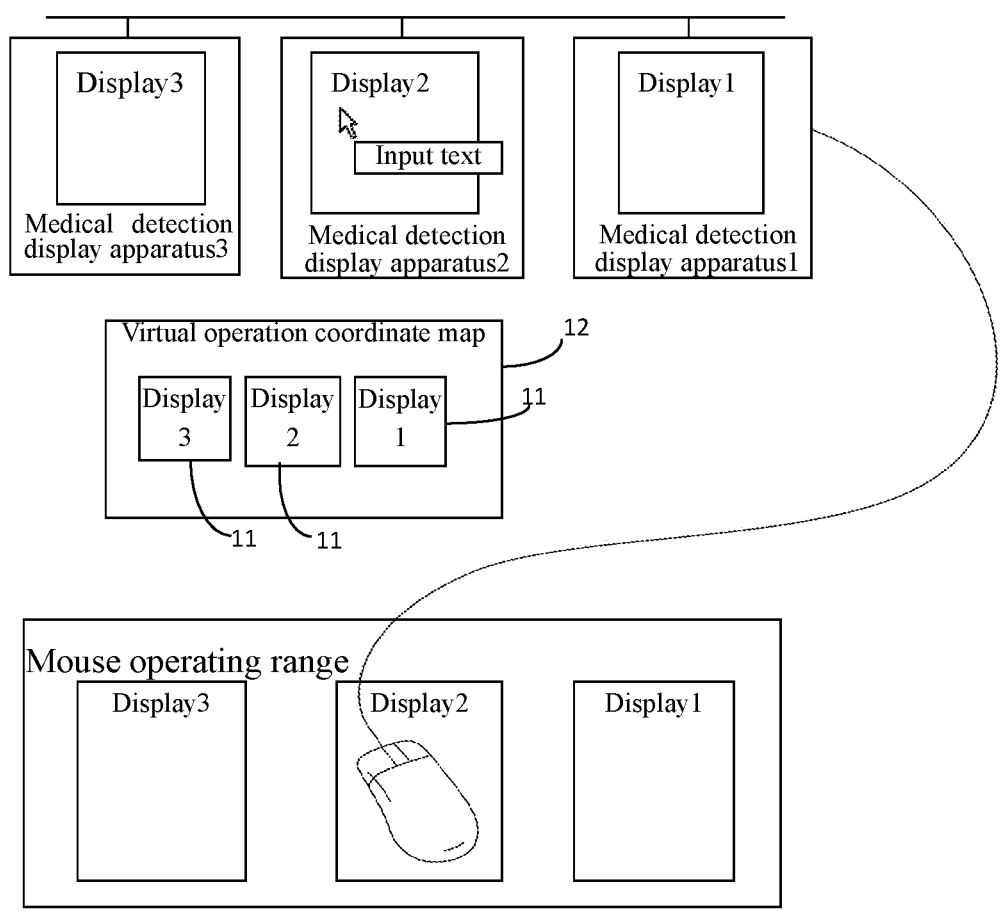
FIG. 7 is a schematic diagram of a manipulation method in an embodiment.

As an example, as shown in FIG. 7, in one embodiment of the present disclosure, the above step S220 includes, according to the display installation position relationships of the plurality of medical detection display apparatuses, forming a virtual operation coordinate map 12 corresponding, on a one-to-one basis, to the display installation position relationship based on an operation attribute of the accessed external input device, each of the medical detection display apparatuses corresponding to a coordinate area 11. The operation attribute of the external input device mentioned herein includes: an actual coordinate measurement range of the mouse movement corresponding to the display, a data measurement range of a graphics tablet, an actual coordinate measurement range corresponding to the scroll wheel, etc. That is to say, the operation attribute of the external input devices refers to an actual coordinate measurement range corresponding to each external input devices according to its own characteristics and used for positioning the cursor.

Hereafter, which coordinate area 11 the motion result of the cursor is located in on the virtual operation coordinate map 12 is sought according to the cursor movement information, and according to the sought coordinate area, the medical detection display apparatus corresponding to the coordinate area 11 is selected from the plurality of medical detection display apparatuses as the specified medical detection display apparatus.

In this embodiment, the position of the cursor is controlled by using the external input device, such as the mouse, so as to determine the different screen specified by the user. The motion result of the cursor in this embodiment includes: the range of motion of the cursor from before to after the movement, the final position of the cursor after the movement, etc.

Figure 8:
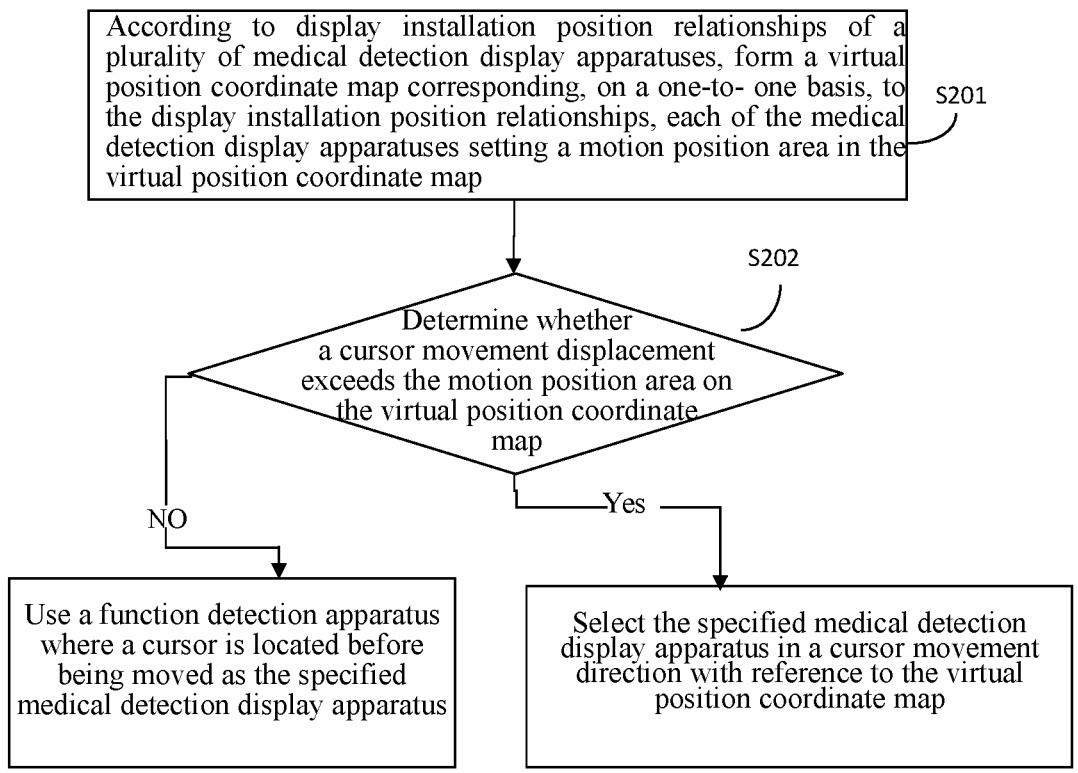
FIG. 8 is a schematic flowchart of a method in an embodiment.
Figure 9:
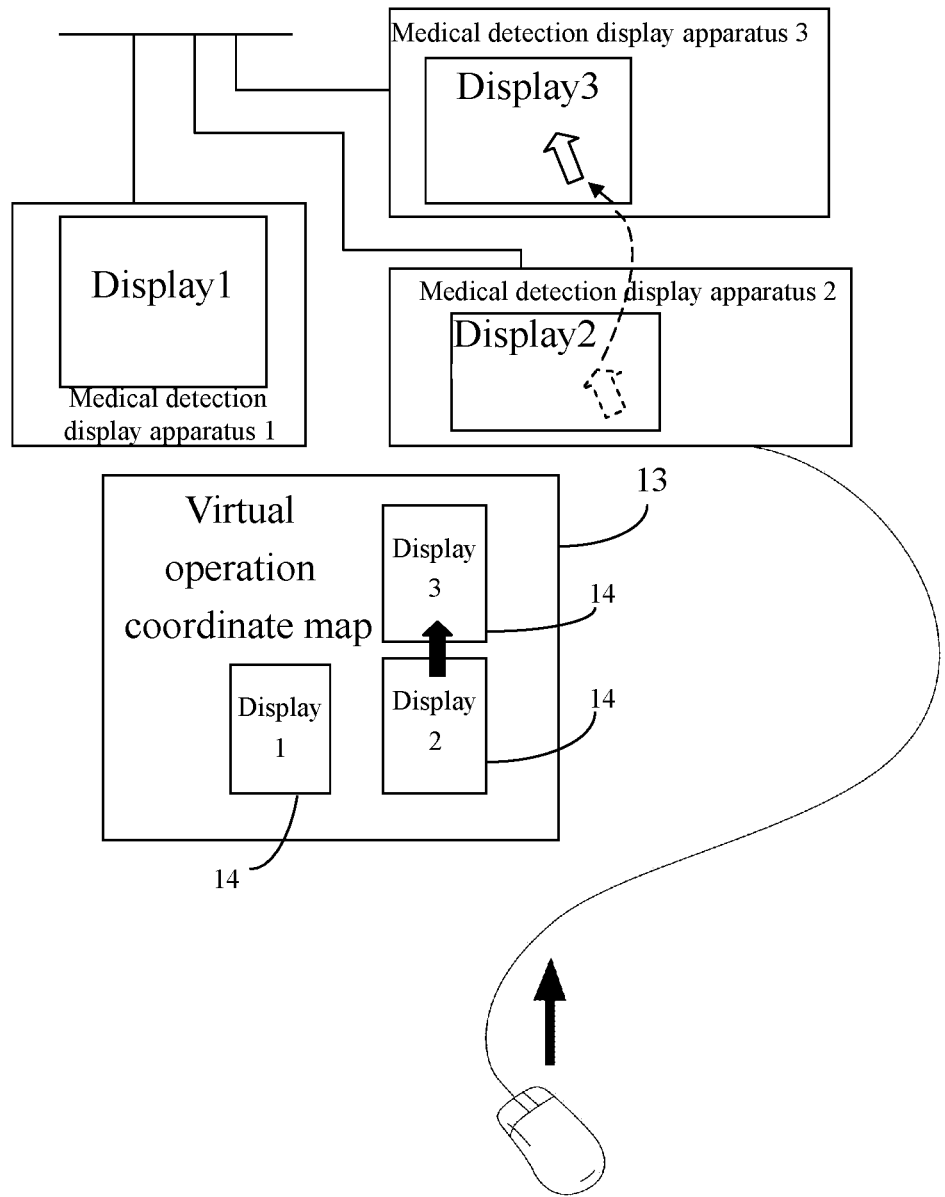
FIG. 9 is a schematic diagram of a manipulation method in the embodiment shown in FIG. 8.

As another example, as shown in FIGS. 8 and 9, in one embodiment of the present disclosure, the above step S220 includes:

Step S201: according to the display installation position relationships of the plurality of medical detection display apparatuses, forming a virtual position coordinate map 13 corresponding, on a one-to-one basis, to the display installation position relationship, each of the medical detection display apparatuses setting a motion position area 14 in the virtual position coordinate map 13. As an example, within the range of 100*100 coordinate area, a motion position range is divided for each of the medical detection display apparatuses in accordance with the display installation position relationships. The motion position ranges for different medical detection display apparatuses may be the same or different.

Step S202, based on the cursor movement information, determining whether the cursor movement displacement exceeds the motion position area. For example, it is determined whether the cursor movement displacement after the movement of the mouse along the long black arrow as shown in FIG. 9 exceeds the corresponding movement position area, on the virtual position coordinate map 13, of the medical detection display apparatus where the cursor is displayed before being moved. If the corresponding motion position areas 14 of all of the medical detection display apparatuses are the same, it may be determined whether the cursor movement displacement exceeds a single motion position area. Therefore, the motion position area in step S202 refers to the corresponding motion position area, on the virtual position coordinate map 13, of the medical detection display apparatus where the cursor is displayed before being moved. Exceeding the motion position area in this embodiment may be exceeding a coordinate range where the motion position area is located in the cursor movement direction, and the coordinate range where the motion position area is located may be a rectangular area formed with defined length and width values, or a circular area with a defined diameter or radius, etc., which will not be enumerated here. Similarly, the medical detection display apparatus where the cursor is displayed before being moved in this embodiment refers to the medical detection display apparatus corresponding to the display interface where the controllable cursor is displayed before the external input device controls the cursor to move same.

If the cursor movement displacement exceeds the aforementioned motion position area, it is possible to refer to the virtual position coordinate map 13, in the cursor movement direction (the short black arrow as shown in FIG. 9), the medical detection display corresponding to the motion position range to which the cursor movement displacement spans is selected as the specified medical detection display apparatus. For example, in FIG. 9, if the threshold of the motion position range is 10 mm in the direction of the black arrow, then when the mouse moves by 15 mm along the black arrow, the virtual position coordinate map 13 spans from the motion position range corresponding to the display 2 to another motion position range corresponding to the display 3 in the cursor movement direction, and the medical detection display apparatus corresponding to the another motion position range is used as the medical detection display apparatus specified by the user. Of course, it is also possible to refer to the virtual position coordinate map 13, in the cursor movement direction (the short black arrow as shown in FIG. 9), the medical detection display apparatus positioned adjacent to the medical detection display apparatus where the cursor is displayed before being moved is selected as the specified medical detection display apparatus. For example, the medical detection display apparatus where the cursor is located before being controlled to move is numbered 2, and the mouse moves in the direction of the black arrow in FIG. 9, then the display 3, namely the medical detection display apparatus 3 is adjacent to the display 2 in the cursor movement direction on the virtual position coordinate map 13. The display of the cursor will jump from the display 2 to the display 3.

If the cursor movement displacement does not exceed the foregoing motion position area, the medical detection display apparatus where the cursor is displayed before being moved is used as the specified medical detection display apparatus.

Of course, if the above-mentioned coordinate map selection method is not used, the following method can also be used. For example, in some embodiments of the present disclosure, the above step S220 may also include the following steps:

first, determining whether the cursor movement speed and/or the cursor movement displacement exceed(s) a predetermined threshold(s), and then, when the cursor movement speed and/or cursor movement displacement exceed(s) the predetermined threshold(s), the medical detection display apparatus installed at a position adjacent to the medical detection display apparatus where the cursor is displayed before being moved is selected in the cursor movement direction as the medical detection display apparatus specified the user. When the cursor movement speed and/or cursor movement displacement do(es) not exceed the predetermined threshold(s), the medical detection display apparatus where the cursor is displayed before being moved is used as the specified medical detection display apparatus. The method of this embodiment is simpler and facilitates operation and computer identification.

Alternatively, the above step S220 may also include the following steps:

first, determining whether the cursor is controlled to move same to a boundary of the current display interface, and if so, continuing to determine whether the cursor movement information still indicates that the cursor is to move in a direction crossing the boundary; otherwise, the medical detection display apparatus where the cursor is displayed before being moved is used as the specified medical detection display apparatus.

When the cursor is controlled to move to a boundary of the current display interface, and the cursor movement information still indicates that the cursor is to move in a direction crossing the boundary, a medical detection display apparatus installed at a position adjacent to the medical detection display apparatus where the cursor is located before movement is selected in the cursor movement direction as the specified medical detection display apparatus; otherwise, it stops and waits for the acquisition of the next cursor movement information.

If the entire medical workstation is activated for the first time, the aforementioned medical detection display apparatus where the cursor is located before being moved may be the medical detection display apparatus connected to the external input device or the medical detection display apparatus where the cursor was displayed before the previous shutdown.

In the above embodiments, several methods for controlling the position of the cursor by using the external input device, such as the mouse, so as to determine the different display screen specified by the user are provided. However, the embodiments of the present disclosure are not limited to the foregoing several methods.

In the converting step S300, the interaction information is converted into a display message matching the display requirements corresponding to the specified medical detection display apparatus. In this step, the interaction information is converted according to the display requirements, such as the display resolution, landscape or portrait screen, the display contents and the display format, of each medical detection display apparatus, to obtain the display information matching the display requirements of each medical detection display apparatus, and the conversion method may use resolution adjustment, display standard adjustment and other common methods. Of course, in order to facilitate seeking, the display requirements corresponding to each medical detection display apparatus may be pre-stored on the storage device.

In addition, in some embodiments of the present disclosure, the converting step S300 further includes: receiving the foregoing shared information, and converting the shared information into a presentation message matching the display requirements corresponding to the specified medical detection display apparatus.

In the searching step S400, information about a transmission path of the specified medical detection display apparatus in the message communication channel is acquired. For the explanation of the transmission path information, reference is made to the forgoing related description.

In order to facilitate searching and seeking, the transmission path information corresponding to each medical detection display apparatus may be stored on the storage device.

In order to facilitate storage and invocation, it may also be maintained in the form of a data list. For example, a correspondence relationship table between identifiers corresponding to all the medical detection display apparatuses and related transmission path information is established and saved. The identifiers corresponding to all the medical detection display apparatuses and the related transmission path information comprise the network communication addresses corresponding to all the medical detection display apparatuses. The identifiers herein are distinguishing marks used by the computer to distinguish the plurality of medical detection display apparatuses and may be any one of numbers, marks, device production labels, etc., or may be directly network communication addresses, communication path information, etc. Of course, they may also comprise the correspondence relationship of the communication device and its related transmission path information during storage, including information about the communication path between the communication device and any one of the medical detection display apparatuses.

In the sending step S500, a transmission message carrying the presentation message and the transmission path information is transmitted to the specified medical detection display apparatus via the message communication channel, to output and display the display message on the specified medical detection display apparatus.

In addition, in some embodiments of the present disclosure, the sending step S500 further includes: transmitting a transmission message carrying the presentation message and the transmission path information to the specified medical detection display apparatus via the message communication channel, to output and display the presentation message on the specified medical detection display apparatus.

For the above-mentioned encapsulation and sending technologies related to messages, reference may be made to the message format usage methods in the prior art, for example, the transmission path information may be encapsulated at the head or tail of the sent message.

The step of transmitting to the specified medical detection display apparatus via the message communication channel includes:

based on the embodiments shown in FIGS. 4A and 4B, sending the transmission message to the message communication channel to achieve the transmission to the specified medical detection display apparatus; or based on the embodiment shown in FIG. 4C, sending the transmission message to the medical detection display apparatus adjacent to itself ("adjacent" herein refers to directly connected to itself) on the message communication channel, to achieve the transmission to the specified medical detection display apparatus by means of forwarding.

In the delivery step S600, for the received transmission message formed in step S500, the display message is output and displayed on the specified medical detection display apparatus.

In addition, in some embodiments of the present disclosure, the delivery step S600 further includes: for the received transmission message formed in step S500, outputting and displaying the presentation message on the specified medical detection display apparatus.

If the specified medical detection display apparatus is the same as the medical detection display apparatus where the cursor is displayed before being moved, there is no switching of the displays. If the specified medical detection display apparatus is not the same as the medical detection display apparatus where the cursor is displayed before being moved, the display message or the presentation message is to be transmitted to the specified medical detection display apparatus via the message communication channel for displaying same.

In the method of FIG. 3, the parsing step S200, the converting step S300, the searching step S400 and the sending step S500 may be performed by a separate device, such as one of the aforementioned plurality of medical detection display apparatus, or a communication device independent of the plurality of medical detection display apparatus. Then, when dealing with the interaction information or the shared information, the corresponding message processing is uniformly completed by such a device in the entire message communication channel, and the information is then distributed to the corresponding medical detection display apparatuses for outputting and displaying same. This device will be referred to as a central machine herein to demonstrate its status for transferring the message in the message communication channel. Therefore, the central machine transmits the display message and/or the presentation message to the specified medical detection display apparatus according to the transmission path information corresponding to the specified medical detection display apparatus when performing the above sending step S500. For example, the transmission message carrying the network communication address corresponding to the specified medical detection display apparatus is sent to a wired network or a wireless network for allowing the other medical detection display apparatus to receive same, so as to transmit the display message and/or the presentation message to the specified medical detection display apparatus. Alternatively, it may also be possible for the transmission message to be forwarded to the corresponding target node through the adjacent medical detection display apparatus or the communication device in sequence according to the communication path information corresponding to the specified medical detection display apparatus.

In one embodiment of the present disclosure, the step of setting the central machine in the message communication channel further includes implementing the startup execution timing of each of the above steps the following ways.

As an example, based on the application scenarios of the solid line box portions in FIGS. 4A to 4C, when the central machine is one of the plurality of medical detection display apparatuses, the central machine allocates the transmission path information corresponding to the other medical detection display apparatuses in the message communication channel, stores the correspondence relationship of the transmission path information and the medical detection display apparatuses, and transmits the message carrying the transmission path information corresponding to the central machine to the other medical detection display apparatus, and the other medical detection display apparatuses respectively receive the message from the central machine and initiate the execution of the above forwarding and delivery steps.

As another example, based on the application scenarios of the solid and dashed line box portions in FIGS. 4A to 4C, when the central machine is the communication device, the central machine allocates the transmission path information corresponding to the plurality of medical detection display apparatuses in the message communication channel, stores the correspondence relationship of the transmission path information and the plurality of medical detection display apparatuses, and transmits the message carrying the transmission path information corresponding to the central machine to the plurality of medical detection display apparatus, and the plurality of medical detection display apparatuses respectively receive the message from the central machine and initiate the execution of the above forwarding and delivery steps.

Based on the application scenarios of the solid line box portions in FIGS. 4A to 4C, in one embodiment of the present disclosure, before the above step S100, one of the pluralities of medical detection display apparatus is set to be the central machine in the following ways.

As an example, first, the medical detection display apparatus connected to the external input receives a coordinated control operation instruction from an external input, and the coordinated control operation instruction may come from an external network, or from an external input device accessing one of the plurality of medical detection display apparatus, or from an information sharing device accessing one of the plurality of medical detection display apparatus;

the medical detection display apparatus then executes the coordinated control operation instruction, sets itself (i.e., the medical detection display apparatus receiving the coordinated detection control instruction) to be the central machine, and sends to the other medical detection display apparatuses a message mechanism establishment command carrying for establishing a message transceiving mechanism in the network; and second, the other medical detection display apparatuses respectively receive the message mechanism establishment command and feed a reply message back to the central machine after execution, so as complete the establishment of communication with the central machine.

As another example, when the external input device or the information sharing device accesses one of the plurality of medical detection display apparatus, the medical detection display apparatus connected to the external input device or the information sharing device is set to be the central machine. Alternatively, it is also possible that one of the plurality of medical detection display apparatuses is specified as the central machine in advance. For example, in one embodiment of the present disclosure, when the external input device accesses one of the plurality of medical detection display apparatus, a prompt box is output and displayed for prompting the user to select whether or not to activate the coordinated operation mode and/or select the central machine. The coordinated operation mode herein refers to a working mode obtained between the plurality of medical detection display apparatuses by performing the method shown in FIG. 3.

In addition, based on the application scenarios of the solid-line box portions in FIGS. 4A to 4C, the central machine is one of the plurality of medical detection display apparatuses. In one embodiment of the present disclosure, before the above forwarding step, the following step may be performed:

determining whether the interaction information or the shared information originates from the external input device accessing the central machine; if yes, the interaction information or the shared information is acquired by the central machine from the external input device or the information sharing device, and is output and displayed on the medical detection display apparatuses where the interaction information or the shared information is located; otherwise, the forwarding step S100 is performed, and the interaction information or the shared information is acquired from one of the medical detection display apparatuses other than the central machine and is forwarded to the central machine. In this embodiment, it is possible to avoid wrong delivery of the message, communication failure, and prolonged message processing time.

For the different mechanisms for forming the message communication channel, the steps of receiving the interaction information, receiving the shared information, or receiving the transmission message involved in the above receiving and delivery steps, in one embodiment of the present disclosure, may be implemented in the following ways:

based on the application scenarios of FIGS. 4A and 4B, the device (including one of the medical detection display apparatuses and the communication device) that currently receives the interaction information, the shared information, or the transmission message determines whether the communication address carried in the message received from the network is consistent with its own network communication address in the network; if yes, it indicates that the device itself is the specified medical detection display apparatus, which receives the message, and outputs and displays the display information or the presentation message, or it indicates that the device itself is the central machine, which receives the message to parse the interaction information or the shared information; otherwise, the received message is discarded. Alternatively, based on the application scenario of FIG. 4C, the device that currently receives the interaction information, the shared information, or the transmission message determines whether the communication path information carried in the received message indicates that the device itself is a target node; if yes, it indicates that the device itself is the specified medical detection display apparatus, which receives the message, and outputs and displays the display information or the presentation message, or it indicates that the device itself is the central machine, which receives the message to parse the interaction information or the shared information; otherwise, the received message is forwarded to the adjacent medical detection display apparatus located on the message communication channel or the communication device, the message including the interaction information, the shared information, or the transmission message, wherein the target node includes: the specified medical detection display apparatus, or the central machine.

In one embodiment of the present disclosure, based on the application scenario of FIG. 4C, the step of determining whether the communication path information carried in the received message indicates that the device itself is a target node in the above steps may comprise one of the following ways:

determining whether the number of times of forwarding required in the process of reaching the target node and included in the communication path information is zero, and if the number of times of forwarding is zero, indicating that the device itself is a target node, otherwise the device itself is a non-target node, and decrementing the number of times of forwarding and embedding same into the message forwarded to the adjacent medical detection display apparatus or the communication device; and determining whether a number corresponding to the target node and included in the communication path information is a number corresponding to the device itself, and if so, indicating that the device itself is a target node, otherwise the device itself is a non-target node.

The combination of the above two ways may also be the simultaneous execution of the above two determinations. If the determination results are both yes, it indicates that the device itself is a target node, otherwise the device itself is a non-target node. This ensures the reliability of reception of the information and prevents the occurrence of information processing errors.

Figure 10:
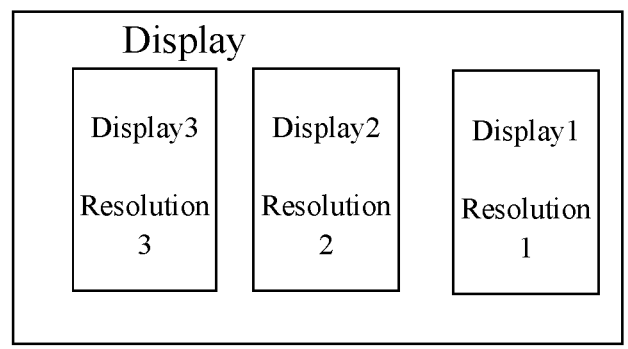
FIG. 10 is a schematic diagram of a display installation position relationship and/or a display requirement corresponding to each medical detection display apparatus displayed in an interface in one embodiment of the present disclosure.

In order to increase the effect of the user experience, and facilitate the user to set and modify the related setting mode freely, as shown in FIG. 10, in one embodiment of the present disclosure, it may also be possible in the method shown in FIG. 3 that one of the plurality of medical detection display apparatuses displays the display installation position relationships of the plurality of medical detection display apparatuses, and/or the display requirements corresponding to each of the medical detection display apparatuses, and acquires a user's configuration instruction data via the external input device, and adjusts the display installation position relationships and/or the display requirements corresponding to each of the medical detection display apparatuses according to the configuration instruction.

In the embodiment shown in FIG. 3, the three function detection devices shown in FIG. 1 may be seamlessly and directly operated no matter the external input device (or control device) is connected to which one of the medical detection display apparatuses, and there is no need to provide any other intermediate hardware switching devices. Of course, the embodiments of the present disclosure are not necessarily limited to a medical workstation having three medical detection display apparatuses, but may also be applied to a medical workstation having a plurality of medical detection display apparatuses.

It may be seen that the method shown in FIG. 3 provides a new message transfer mechanism related to the external input device and the information sharing device. By means of this message transfer mechanism, control input interfaces of the interconnected plurality of medical detection display apparatuses are unified, and the interface interaction and information display of any one of the medical detection display apparatuses may be realized by means of one external input device and information sharing device.

With reference to the respective flowchart in FIG. 3, it should be understood that the various steps in the figure are sequentially displayed as indicated by the arrows, but the steps are not necessarily performed in the order indicated by the arrows. Unless expressly described herein, the execution of these steps is not limited to a strict order, instead, the steps may be executed in another order. Moreover, at least some of the steps in the figure may comprise a plurality of sub-steps or a plurality of phases, and these sub-steps or phases are not necessarily performed at the same time.

In addition, in the above description of the method shown in FIG. 3, variations, developments and extensions are made on the embodiment shown in FIG. 3, to obtain a plurality of embodiments. The technical features disclosed in these embodiments may be combined with each other, and the combined technical solutions are all within the scope disclosed by the description of the present disclosure.

Figure 11A:
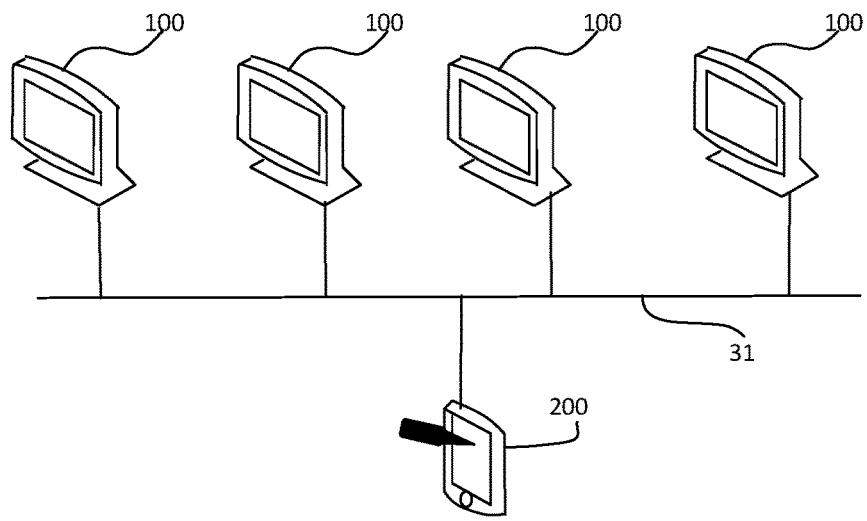
FIGS. 11A, 11B and 11C are schematic structural diagrams of multiple methods for implementing a coordinated operation mode using a communication device.
Figure 11B:
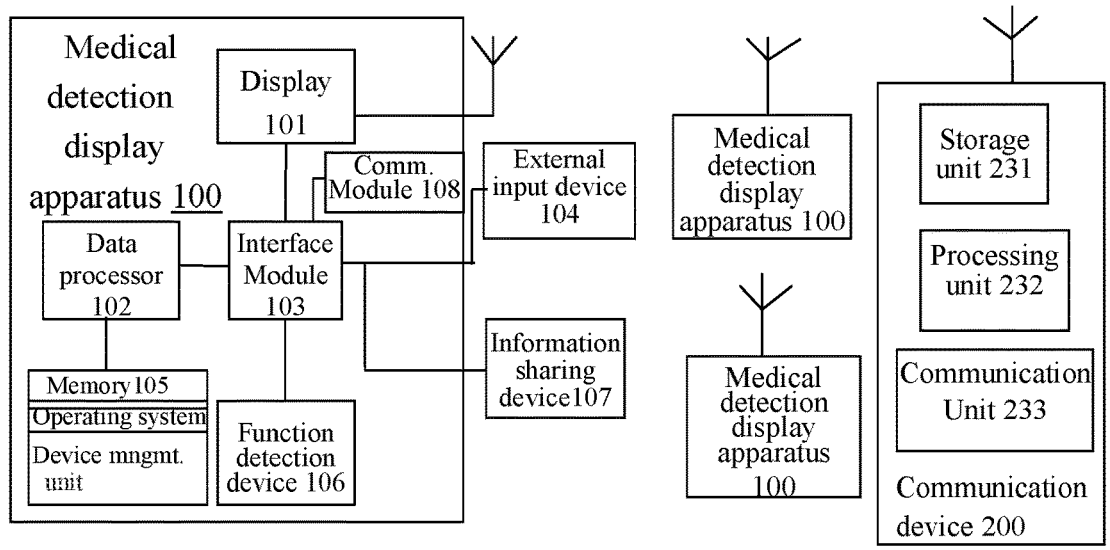
Figure 11C:
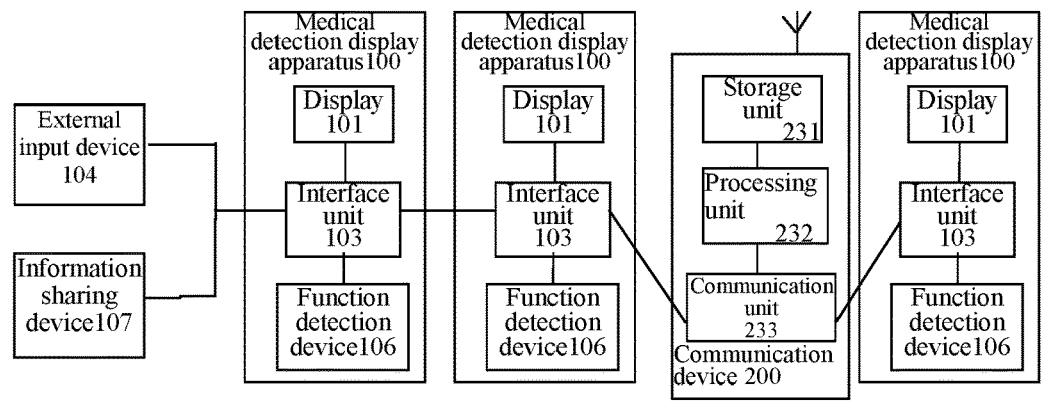

Based on the system control method shown in FIG. 3, in one embodiment of the present disclosure, there is shown a communication device, and the method for accessing a plurality of medical detection display apparatuses by the communication device to form a message communication channel refers to the related structures and their description shown in FIGS. 4A to 4C. As shown in FIG. 11A, this communication device 200 may be used to execute the parsing step S200, the converting step S300, the sending step S500, and the searching step S400 in the method shown in FIG. 3, and may also execute the receiving step S101. A connection line 31 for the plurality of medical detection display apparatuses 100 and the communication device 200 in FIG. 11A may be a wireless network connection, a wired network connection, a hardware interface connection line or the like. This communication device 200 is independent of the plurality of medical detection display apparatuses 100. When this communication device is accessed, the coordinated operation mode between the plurality of medical detection display apparatuses may be initiated. The communication device may access a network formed by connecting a plurality of medical detection display apparatuses in a wireless or wired manner (as shown in FIG. 11B), or may access any one of the plurality of medical detection display apparatuses via a hardware interface (as shown in FIG. 11C).

Therefore, in one embodiment of the present disclosure, a communication device may be provided, which may be any electronic product, such as a mobile phone or an IPAD. The communication device may be used for accessing a message communication channel formed by a plurality of medical detection display apparatuses. As shown in FIGS. 11B and 11C, the communication device 200 in this embodiment may comprise a storage unit 231, a communication unit 233, and a processing unit 232.

The storage unit 231 is configured to pre-store correspondence relationships between identifiers corresponding to the plurality of medical detection display apparatuses, and information about transmission paths of the plurality of medical detection display apparatuses in the message communication channel and corresponding display requirements. The identifiers corresponding to the plurality of medical detection display apparatuses are distinguishing marks used by the computer to distinguish the plurality of medical detection display apparatuses and may be any one of numbers, marks, device production labels, corresponding coordinate areas in a coordinate map, etc., or may be directly network communication addresses, communication path information, etc. The transmission path information includes: a corresponding network communication address of each of the medical detection display apparatuses and the communication device in a network when the message communication channel is formed by means of the network, or information about a communication path between each of the medical communication display devices and the communication device when the message communication channel is formed by means of the serial connection via hardware interfaces. For detailed explanation of the transmission path information and the corresponding display requirements, reference may be made to the forgoing related description.

The communication unit 233 is configured to receive external interaction information acquired from an external input device accessing one of the plurality of medical detection display apparatuses. The communication unit 233 herein may be a hardware interface adapted to an interface unit of the medical detection display apparatus. As shown in FIG. 11C, the communication unit 233 may be directly connected to the medical detection display apparatus via the hardware interface. Alternatively, the communication unit 233 may be a wireless Wi-Fi interface chip, a 3G network interface chip, a 4G network interface chip, etc. When the medical detection display apparatus forwards the interaction information via the message communication channel, the communication device 200 receives the interaction information via the communication unit 233.

The processing unit 232 is configured to parse the interaction information to obtain an identifier corresponding to a medical detection display apparatus specified by a user, and convert the interaction information into a display message matching the specified medical detection display apparatus according to a display requirement. The processing unit 232 is configured to execute the above parsing step S200 and converting step S300. For the specific implementations, reference may be made to the forgoing related description.

The communication unit 233 is further configured to obtain, according to the identifier, information about a transmission path of the specified medical detection display apparatus in the message communication channel, and transmit a transmission message carrying the display message and the transmission path information to the specified medical detection display apparatus via the message communication channel. The process of transmitting to the specified medical detection display apparatus via the message communication channel includes sending the transmission message to the network based on FIG. 11B, or transferring the transmission message to the specified medical detection display apparatus through the adjacent medical detection display apparatuses in sequence based on FIG. 11C. As an example, based on the embodiment shown in FIG. 11C, when the communication device 200 wants to send the transmission message to the left first medical detection display apparatus, the transmission message needs to be relayed by the left second medical detection display apparatus, and the sending path is then as follows: the transmission message is sent from the communication device 200, through the left second medical detection display apparatus, and then to the left first medical detection display apparatus. The communication unit 233 is configured to execute the receiving step S101, the searching step S400, and the sending step S500 in the method shown in FIG. 3, and therefore, for the specific implementation thereof, reference may be made to the foregoing description related to the receiving step S101, the searching step S400, and the sending step S500.

Further, in one embodiment of the present disclosure, the communication unit 233 is further configured to receive external shared information obtained from an information sharing device accessing one of the plurality of medical detection display apparatuses; the processing unit 232 is further configured to convert the shared information into a presentation message matching a display requirement corresponding to the specified medical detection display apparatus; and the communication unit 233 is further configured to transmit a transmission message carrying the presentation message and the transmission path information to the specified medical detection display apparatus via the message communication channel.

When the communication device 200 receives the interaction information or the shared information from the message communication channel, based on the embodiment shown in FIG. 11B, the communication unit 233 also practices the reception of the interaction information by determining whether the communication address carried in the message received from the network is consistent with its own network communication address in the network, if yes, receiving the message, otherwise discarding the received message. Alternatively, based on the embodiment shown in FIG. 11C, the communication unit 233 also practices the reception of the interaction information by determining whether the communication path information carried in the received message indicates that the communication unit itself is a target node; if yes, receiving the message, otherwise, forwarding the received message to the adjacent medical detection display apparatus.

In addition, the communication unit 233 is further configured to determine whether the communication path information carried in the received message indicates that the communication unit itself is a target node in one of the following ways:

determining whether the number of times of forwarding required in the process of reaching the target node and included in the communication path information is zero, and if the number of times of forwarding is zero, indicating that the communication unit itself is a target node, otherwise the communication unit itself is a non-target node, and decrementing the number of times of forwarding and embedding same into the message to forward same to the adjacent medical detection display apparatus; and determining whether a number corresponding to the target node and included in the communication path information is a number corresponding to the communication unit, and if so, indicating that the communication unit itself is a target node.

In one embodiment of the present disclosure, the processing unit 232 parses the interaction information to obtain the identifier corresponding to the medical detection display apparatus specified by the user in the following way: first, identifying cursor movement information in the interaction information; and then acquiring a specified medical detection display apparatus selected from the plurality of medical detection display apparatuses by the user according to the cursor movement information, and outputting the identifier corresponding to the specified medical detection display apparatus. For specific details in this embodiment, reference may be made to the foregoing description related to the parsing step S200, which is not described herein again.

In one embodiment of the present disclosure, when the communication device 200 accesses the message communication channel formed by the plurality of medical detection display apparatuses 100, the processing unit 232 generates a prompt message for prompting the user to select whether to initiate a coordinated operation mode. The communication unit transmits the prompt message to one of the plurality of medical detection display apparatuses for outputting and displaying same. Alternatively, the communication device 200 further includes a display unit, which may be various types of display devices, such as a touch screen display, a 3D display device, and a 2D display. The processing unit 232 generates a prompt message for prompting the user to select whether to initiate the coordinated operation mode, and outputs same to a display unit carried by the processing unit itself for outputting and displaying same.

Based on the above embodiments, it may be seen that, when the coordinated operation mode between medical detection devices provided by the present disclosure is implemented, new hardware devices may be necessarily added, or it may also be implemented through the combination of software and hardware without adding new hardware devices, thereby reducing the cost of improvement in implementing the coordinated control between medical detection devices, without the need to improve the hardware of the plurality of medical detection display apparatuses themselves, and facilitating the implementation of coordinated control between medical detection devices provided by multiple companies and between multiple types of medical detection devices.

Based on the method shown in FIG. 3, in order to facilitate the implementation of the message transfer mechanism described above, and to reduce the cost of improvement, the system for controlling coordination between medical devices obtained using the above technique is implemented on the plurality of medical detection display apparatuses 100. In one embodiment of the present disclosure, the system for controlling coordination between medical devices includes: a plurality of message transceiving units 202 and a coordination message processing unit 203. The coordination message processing unit 203 is configured to execute the parsing step S200 and the converting step S300 in the method shown in FIG. 3 described above.

The message transceiving unit 202 may be configured to implement the respective functions in the forwarding step S100, the receiving step S101, the searching step S400, the sending step S500, and the delivering step S600 in the method shown in FIG. 3 described above. Specifically, the following ways may be used:

1. Each of the message transceiving units 202 is configured to be able to execute the forwarding step S100, the receiving step S101, the searching step S400, the sending step S500, and the delivering step S600 in the method shown in FIG. 3 described above.

2. The message transceiving unit 202 connected to the coordination message processing unit 203 is configured to be able to execute the functions of the forwarding step S100, the receiving step S101, the searching step S400, the sending step S500, and the delivering step S600 in the method shown in FIG. 3 described above, whereas the message transceiving units 202 that are not connected to the coordination message processing unit 203 are configured to be able to execute the forwarding step S100 and the delivery step S600 in the method shown in FIG. 3 described above.

3. The message transceiving unit 202 connected to the coordination message processing unit 203 is configured to be able to execute the functions of the receiving step S101, the searching step S400 and the sending step S500 in the method shown in FIG. 3 described above, whereas the message transceiving units 202 that are not connected to the coordination message processing unit 203 are configured to be able to execute the forwarding step S100 and the delivery step S600 in the method shown in FIG. 3 described above.

In addition to the aforementioned three configurations, corresponding functions may also be specifically configured according to the connection relationship between the plurality of message transceiving units 202 and the coordination message processing unit 203. Based on the aforementioned various configuration situations of the plurality of message transceiving units 202 and the coordination message processing unit 203, when the coordinated control between medical devices is implemented between the pluralities of medical detection display apparatuses, and when a coordinated operation mode is obtained, in one embodiment of the present disclosure, the system for controlling coordination between medical devices includes:

a plurality of message transceiving units 202, a message communication channel being provided between the plurality of message transceiving units; and a coordination message processing unit 203 connected to one of the plurality of message transceiving units.

The message transceiving units 202, which are respectively provided corresponding to the plurality of medical detection display apparatuses 100, are configured to acquire interaction information from an external input device accessing the medical detection display apparatuses and forward the interaction information to the coordination message processing unit 203;

the coordination message processing unit 203 is configured to receive the interaction information from the message transceiving unit 202 connected thereto, parse the interaction information to obtain an identifier corresponding to a medical detection display apparatus specified by a user, and convert, according to a display requirement corresponding to the identifier, the interaction information into a display message M2 matching the specified medical detection display apparatus; and the message transceiving unit 202 connected to the coordination message processing unit 203 is configured to acquire, based on the identifier, information about a transmission path of the specified medical detection display apparatus in the message communication channel, and transmit a transmission message carrying the display message and the transmission path information to the message transceiving unit 202 provided corresponding to the specified medical detection display apparatus via the message communication channel, so that the message transceiving unit 202 receives the transmission message M4, and the display message is output and displayed on the specified medical detection display apparatus.

In addition, in one embodiment of the present disclosure, each of the message transceiving units 202 is further configured to forward shared information, which is acquired by the medical detection display apparatus 100 provided corresponding to the message transceiving unit from an accessed information sharing device, to the coordination message processing unit 203; the coordination message processing unit 203 is further configured to receive the shared information from the message transceiving unit 202 connected thereto, and convert the shared information into a presentation message matching the specified medical detection display apparatus; and the message transceiving unit 202 connected to the coordination message processing unit 203 is configured to transmit a transmission message carrying the presentation message M6 and the transmission path information to the message transceiving unit 202 provided corresponding to the specified medical detection display apparatus via the message communication channel, so that the message transceiving unit 202 receives the transmission message, and the presentation message M6 is output and displayed on the specified medical detection display apparatus.

The transmission path information mentioned in this embodiment includes: a corresponding network communication address of the respective message transceiving unit corresponding to each medical detection display apparatus in the network, or information about a communication path between the respective message transceiving unit corresponding to each medical detection display apparatus and the message transceiving unit connected to the coordination message processing unit. The corresponding network communication address of the message transceiving unit in the network and the communication path information may be understood as a medical detection display apparatus provided corresponding to the message transceiving unit.

According to the differences in the respective connection of the plurality of message transceiving units 202 and the coordination message processing unit 203 with the plurality of medical detection display apparatuses and in the architecture of the message communication channel, different specific implementations will be presented. The connection relationship and signal processing flow in each embodiment will be described in detail below with reference to the accompanying drawings.

Figure 12A:
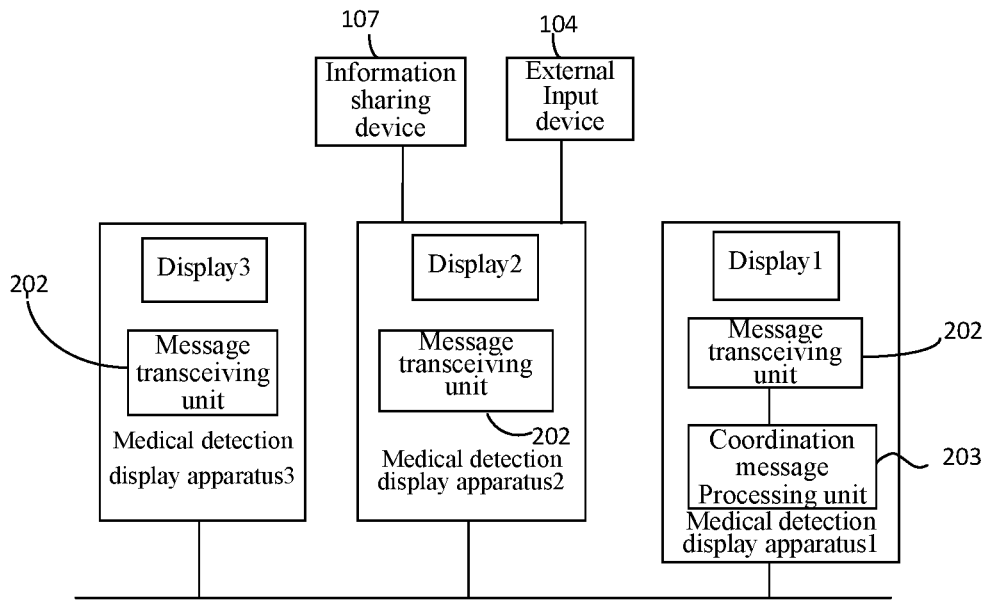
FIG. 12A is a schematic structural diagram of one embodiment of a system for controlling coordination between medical devices.

In the embodiment shown in FIG. 12A, a message transceiving unit 202 is provided on each of medical detection display apparatuses 100, and a coordination message processing unit 203 is provided in least in one of the plurality of medical detection display apparatus. Of course, it may also be possible to provide a plurality of coordination message processing units 203, but in the same period of time, one coordination message processing unit 203 may be activated for performing unified processing and parsing of messages in the message communication channel, that is, performing the functions of the aforementioned central machine. Assume that as shown in FIG. 12A, the coordination message processing unit 203 is provided on the medical detection display apparatus 1, and the medical detection display apparatuses 1 to 3 are respectively provided with a message transceiving unit 202. The medical detection display apparatuses 1 to 3 are corresponding provided with displays 1 to 3. A message communication channel is formed between the plurality of medical detection display apparatus. For the formation of the message communication channel, reference may be made to the forgoing related description.

Figure 12B:
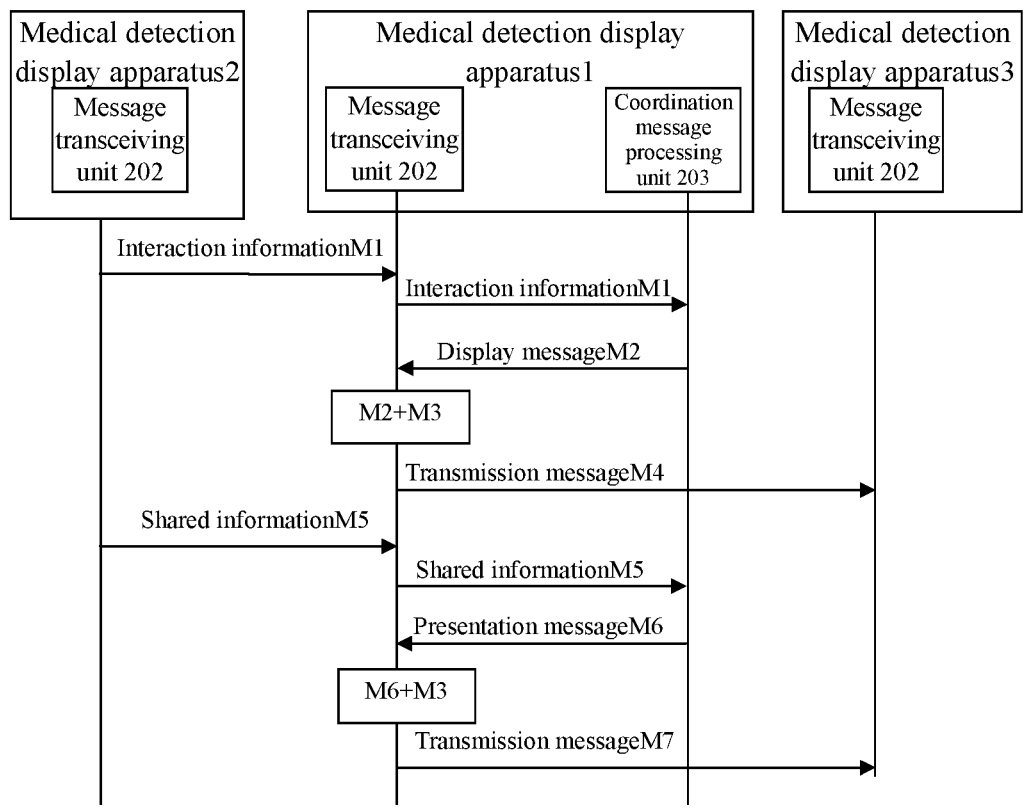
FIGS. 12B and 12C are schematic signal flowcharts of the architecture of FIG. 12A.

FIG. 12B provides an illustrative signal flow of a network-based message communication channel in the embodiment shown in FIG. 12A. The specific flow is as follows.

1. The message transceiving unit 202 on the medical detection display apparatus 2 forwards to the coordination message processing unit 203 the interaction information M1 acquired from the accessed external input device by the medical detection display apparatus 100 provided corresponding to the message transceiving unit.

2. The coordination message processing unit 203 on the medical detection display apparatus 1 receives the interaction information M1 from the message transceiving unit 202 connected thereto, parses the interaction information M1 to obtain an identifier corresponding to a medical detection display apparatus specified by a user, and converts, according to a display requirement corresponding to the identifier, the interaction information M1 into a display message M2 matching the specified medical detection display apparatus. In this embodiment, it is assumed that the specified medical detection display apparatus corresponds to the medical detection display apparatus 3.

3. The message transceiving unit 202 connected to the coordination message processing unit 203 and located on the medical detection display apparatus 1 obtains, based on the identifier, information about a transmission path of the specified medical detection display apparatus in the message communication channel, i.e., the transmission path information corresponding to the medical detection display apparatus 3, and transmits a transmission message M4 carrying the display message M2 and the transmission path information M3 to the message transceiving unit 202 provided corresponding to the medical detection display apparatus 3 via the message communication channel. In this embodiment, the transmission message M4 is forwarded to the message transceiving unit 202 provided corresponding to the medical detection display apparatus 3 by sending the transmission message M4 to the network.

4. The message transceiving unit 202 provided corresponding to the medical detection display apparatus 3 receives the transmission message M4, and the display message M2 is output and displayed on the display 3 corresponding to the medical detection display apparatus 3.

5. The message transceiving unit 202 on the medical detection display apparatus 2 forwards to the coordination message processing unit 203 shared information M5 acquired from the accessed information sharing device by the medical detection display apparatus 100 provided corresponding to the message transceiving unit.

6. The coordination message processing unit 203 on the medical detection display apparatus 1 further receives the shared information M5 from the message transceiving unit 202 connected thereto, and converts the shared information M5 into a presentation message M6 matching the specified medical detection display apparatus.

7. The message transceiving unit 202 connected to the coordination message processing unit 203 and located on the medical detection display apparatus 1 transmits a transmission message M7 carrying the presentation message M6 and the transmission path information M3 to the message transceiving unit 202 provided corresponding to the medical detection display apparatus 3 via the message communication channel.

8. The message transceiving unit 202 provided corresponding to the medical detection display apparatus 3 receives the transmission message M7, and the presentation message M6 is output and displayed on the display 3 corresponding to the medical detection display apparatus 3.

The transmission path information M3 in this embodiment may be the network communication address of the message transceiving unit 202 connected to the coordination message processing unit 203 in the message communication channel, i.e., the network communication address corresponding to the medical detection display apparatus 3. In one embodiment of the present disclosure, the message transceiving units 202 respectively provided corresponding to the plurality of medical detection display apparatuses 100 embed the network communication address of the message transceiving unit connected to the coordination message processing unit in the network into the interaction information or the shared information, and send same to the network to forward the interaction information or the shared information to the coordination message processing unit 203.

Figure 12C:
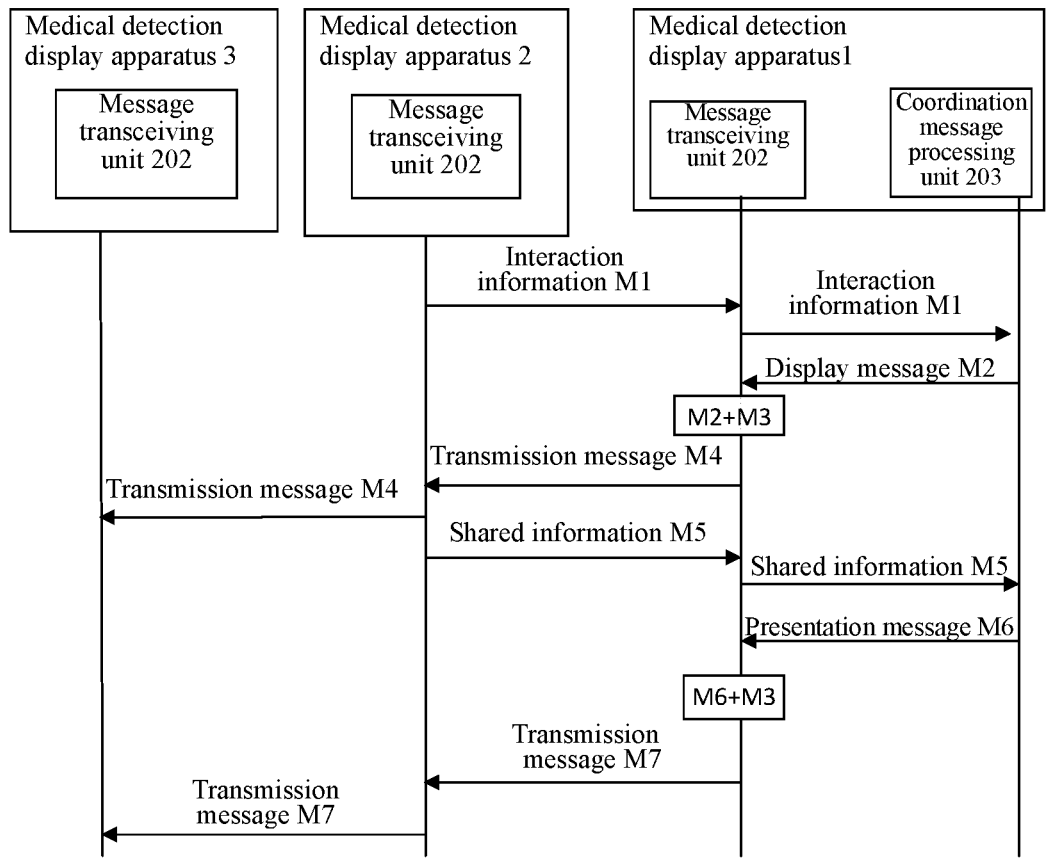

FIG. 12C provides an illustrative signal flow of a non-network-based message communication channel in the embodiment shown in FIG. 12A. That is, the plurality of medical detection display apparatuses 100 are connected together in series via hardware interfaces. The specific flow is as follows. In order to simplify the description of the flow, the processes of forming various messages in the various steps will be simplified. For the specific information, reference may be made to in the foregoing description, so as to highlight the message forwarding process. This is the case in the following description.

1. The message transceiving unit 202 on the medical detection display apparatus 2 forwards to the coordination message processing unit 203 the interaction information M1 acquired from the accessed external input device by the medical detection display apparatus 100 provided corresponding to the message transceiving unit itself. The forwarding mode is directly forwarding the information to the adjacent medical detection display apparatus 1, and receiving the information by the message transceiving unit 202 on the medical detection display apparatus 1.

2. The coordination message processing unit 203 on the medical detection display apparatus 1 receives the interaction information M1 from the message transceiving unit 202 connected thereto, and converts the interaction information M1 into the display message M2. In this embodiment, it is assumed that the specified medical detection display apparatus corresponds to the medical detection display apparatus 3.

3. the message transceiving unit 202 connected to the coordination message processing unit 203 and located on the medical detection display apparatus 1 acquires, based on the identifier, information about a transmission path of the specified medical detection display apparatus in the message communication channel, i.e., the transmission path information corresponding to the medical detection display apparatus 3, forwards a transmission message M4 carrying the display message M2 and the transmission path information M3 to the message transceiving unit 202 located on the adjacent medical detection display apparatus 2 on the message communication channel, and then re-forwards same to the message transceiving unit 202 provided corresponding to the medical detection display apparatus 3 through the message transceiving unit 202 provided on the medical detection display apparatus 2.

4. The message transceiving unit 202 provided corresponding to the medical detection display apparatus 3 receives the transmission message M4, and the display message M2 is output and displayed on the display 3 corresponding to the medical detection display apparatus 3.

5. The message transceiving unit 202 on the medical detection display apparatus 2 forwards to the coordination message processing unit 203 shared information M5 acquired from the accessed information sharing device by the medical detection display apparatus 100 provided corresponding to the message transceiving unit itself.

6. The coordination message processing unit 203 on the medical detection display apparatus 1 further receives the shared information M5 from the message transceiving unit 202 connected thereto, and converts the shared information M5 into a presentation message M6.

7. The message transceiving unit 202 connected to the coordination message processing unit 203 and located on the medical detection display apparatus 1 forwards a transmission message M7 carrying the presentation message M6 and the transmission path information M3 to the message transceiving unit 202 provided on the adjacent medical detection display apparatus 2 on the message communication channel, and then re-forwards same to the message transceiving unit 202 through the message transceiving unit 202 provided on the medical detection display apparatus 2.

8. The message transceiving unit 202 provided corresponding to the medical detection display apparatus 3 receives the transmission message M7, and the presentation message M6 is output and displayed on the display 3 corresponding to the medical detection display apparatus 3.

The transmission path information M3 in this embodiment may be the information of a communication path of the message transceiving unit 202 connected to the coordination message processing unit 203 in the message communication channel, i.e., the network communication address corresponding to the medical detection display apparatus 1 to the medical detection display apparatus 3. In one embodiment of the present disclosure, the message transceiving units 202 respectively provided corresponding to the plurality of medical detection display apparatuses 100 embed the communication path information into the interaction information or the shared information, and forward same to the adjacent message transceiving unit located on the message communication channel to forward the interaction information or the shared information to the coordination message processing unit. The communication path information is information about a communication path between this message transceiving unit and the message transceiving unit connected to the coordination message processing unit.

Figure 13A:
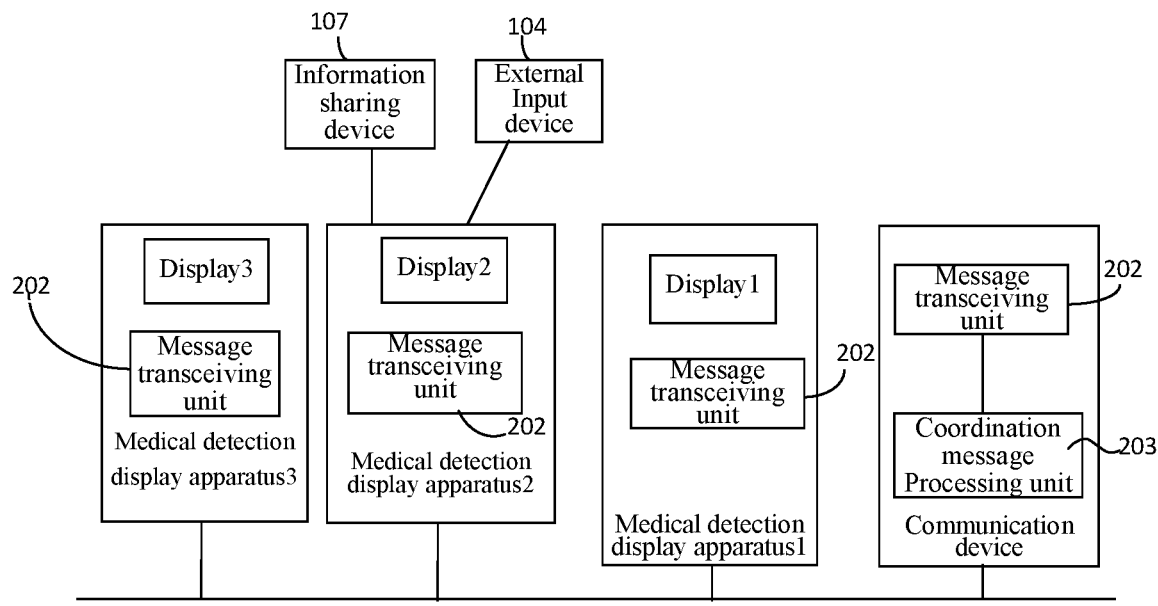
FIG. 13A is a schematic structural diagram of one embodiment of a system for controlling coordination between medical devices.

FIG. 13A provides one embodiment of another connection system architecture. In this embodiment, a message transceiving unit 202 is provided on each of the medical detection display apparatuses 100, and the coordination message processing unit 203 and a message transceiving unit connected thereto are provided on a communication device 210 independent of the plurality of medical detection display apparatuses. The communication device 210 is connected to the plurality of medical detection display apparatuses to form a network to access the message communication channel, or the communication device 210 is connected to one of the plurality of medical detection display apparatuses via a hardware interface to access the message communication channel. The communication device 210 in this embodiment may be the communication device 200 mentioned in the above embodiments. The message transceiving unit 202 on the communication device 210 is configured to be able to execute the functions of the receiving step S101, the searching step S400 and the sending step S500 in the method shown in FIG. 3 described above, whereas the coordination message processing unit 203 is configured to execute the parsing step S200 and the converting step S300 in the method shown in FIG. 3 described above.

Figure 13B:
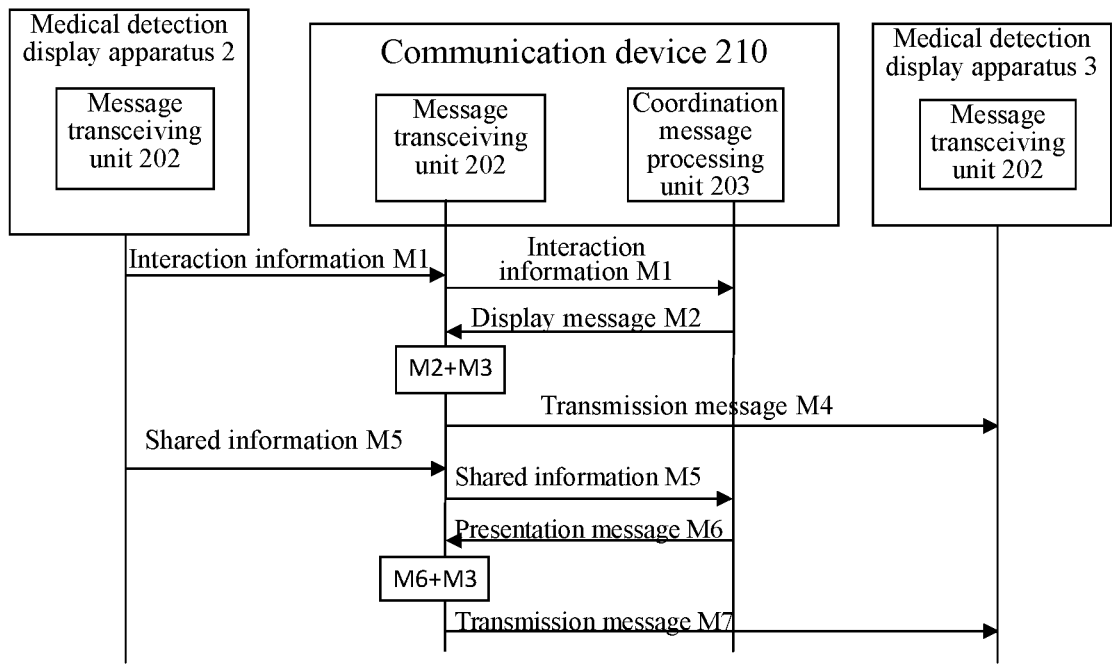
FIGS. 13B and 13C are schematic signal flowcharts of the architecture of FIG. 13A.

FIG. 13B provides an illustrative signal flow of a network-based message communication channel in the embodiment shown in FIG. 13A. The difference from FIG. 12B is that the medical detection display apparatus 1 in FIG. 12B is replaced by the communication device 210, and the detailed description of the flow shown in FIG. 13B will not be repeated here, and reference may be made to the forgoing related description.

Figure 13C:
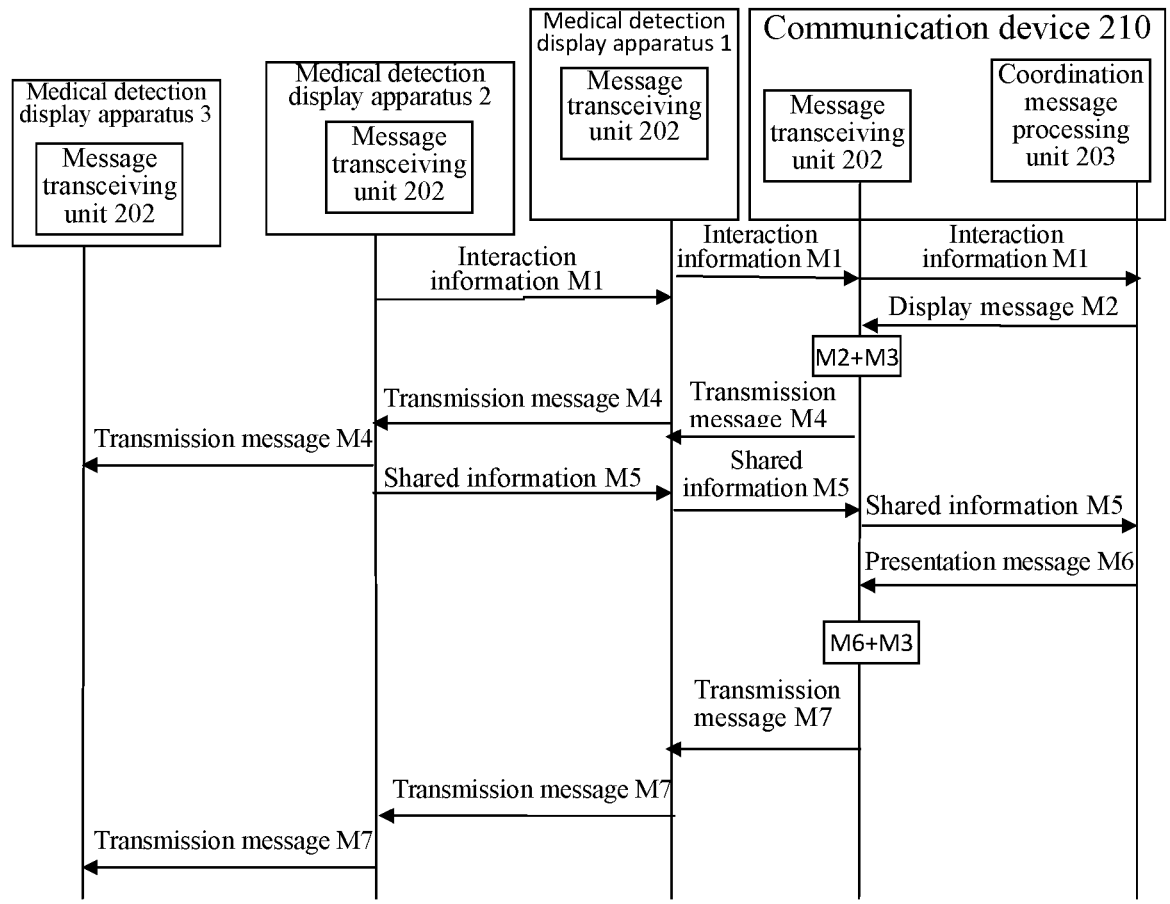

FIG. 13C provides an illustrative signal flow of a non-network-based message communication channel in the embodiment shown in FIG. 13A. That is, the plurality of medical detection display apparatuses 100 are connected together in series via hardware interfaces. The specific flow is as follows.

1. The message transceiving unit 202 on the medical detection display apparatus 2 forwards to the coordination message processing unit 203 the interaction information M1 acquired from the accessed external input device by the medical detection display apparatus 100 provided corresponding to the message transceiving unit itself. The forwarding mode is: forwarding the information to the adjacent medical detection display apparatus 1, and then forwarding the information to the message transceiving unit 202 on the communication device 210 from the message transceiving unit 202 on the medical detection display apparatus 1.

2. The coordination message processing unit 203 on the communication device 210 receives the interaction information M1 from the message transceiving unit 202 connected thereto, and converts the interaction information M1 into a display message M2. In this embodiment, it is assumed that the specified medical detection display apparatus corresponds to the medical detection display apparatus 3.

3. The message transceiving unit 202 connected to the coordination message processing unit 203 and located on the communication device 210 acquires, based on the identifier, transmission path information M3 corresponding to the medical detection display apparatus 3, forwards a transmission message M4 carrying the display message M2 and the transmission path information M3 to the message transceiving unit 202 provided on the adjacent medical detection display apparatus 1 on the message communication channel, and then forwards same to the message detection unit 202 provided corresponding to the medical detection display apparatus 3 through the message transceiving unit 202 provided on the medical detection display apparatus 1 and the message transceiving unit 202 provided on the medical detection display apparatus 2 in sequence.

4. The message transceiving unit 202 provided corresponding to the medical detection display apparatus 3 receives the transmission message M4, and the display message M2 is output and displayed on the display 3 corresponding to the medical detection display apparatus 3.

5. The message transceiving unit 202 on the medical detection display apparatus 2 forwards to the coordination message processing unit 203 shared information M5 acquired from the accessed information sharing device by the medical detection display apparatus 100 provided corresponding to the message transceiving unit itself, including forwarding same to the message transceiving unit 202 on the communication device 210 through the message transceiving unit 202 on the medical detection display apparatus 1.

6. The coordination message processing unit 203 on the communication device 210 further receives the shared information M5 from the message transceiving unit 202 connected thereto, and converts the shared information M5 into a presentation message M6.

7. the message transceiving unit 202 connected to the coordination message processing unit 203 and located on the communication device 210 forwards a transmission message M7 carrying the presentation message M6 and the transmission path information M3 to the message transceiving unit 202 provided on the adjacent medical detection display apparatus 1 on the message communication channel, and then forwards same to the message transceiving unit 202 provided corresponding to the medical detection display apparatus 3 through the message transceiving unit 202 provided on the medical detection display apparatus 1 and the message transceiving unit 202 provided on the medical detection display apparatus 2 in sequence.

8. The message transceiving unit 202 provided corresponding to the medical detection display apparatus 3 receives the transmission message M7, and the presentation message M6 is output and displayed on the display 3 corresponding to the medical detection display apparatus 3.

The transmission path information M3 in this embodiment may be the information of a communication path of the message transceiving unit 202 connected to the coordination message processing unit 203 in the message communication channel, i.e., the network communication address corresponding to the communication device 210 to the medical detection display apparatus 3.

Figure 14:
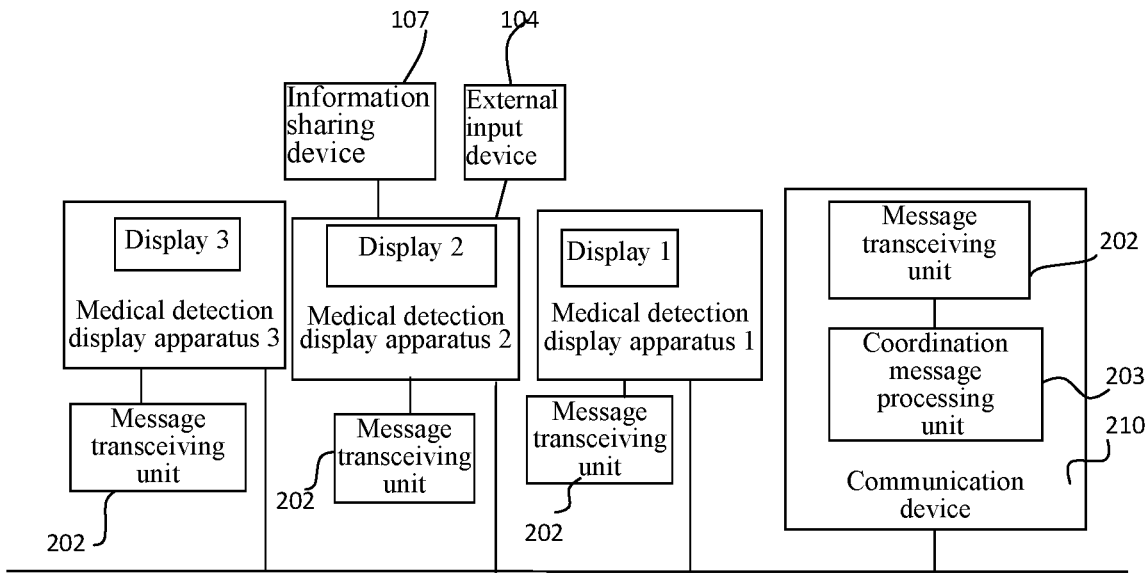
FIGS. 14, 15, 16, 17 and 18 are schematic structural diagrams of various embodiments of a system for controlling coordination between medical devices.

FIG. 14 provides one embodiment of another connection system architecture. In this embodiment, each medical detection display apparatus 100 is correspondingly connected to a message transceiving unit 202. The message transceiving unit 202 herein may be an independent hardware device, and is connected to the medical detection display apparatus 100 via an interface matching an interface unit of the medical detection display apparatus 100, or may also be connected to the medical detection display apparatus 100 via a wireless network (such as Bluetooth, and Wi-Fi). The coordination message processing unit 203 and a message transceiving unit connected thereto are provided on a communication device 210 independent of the plurality of medical detection display apparatuses. The communication device 210 is connected to the plurality of medical detection display apparatuses to form a network to access the message communication channel, or the communication device 210 is connected to one of the plurality of medical detection display apparatuses via a hardware interface to access the message communication channel. The communication device 210 in this embodiment may be the communication device 200 mentioned in the above embodiments. The message transceiving unit 202 on the communication device 210 is configured to be able to execute the functions of the receiving step S101, the searching step S400 and the sending step S500 in the method shown in FIG. 3 described above, whereas the coordination message processing unit 203 is configured to execute the parsing step S200 and the converting step S300 in the method shown in FIG. 3 described above.

Based on the system connection relationship shown in FIG. 14, the signal flow of the networked message communication channel is shown in FIG. 13B, and the signal flow of the non-networked message communication channel formed by connecting the plurality of medical detection display apparatus 100 together in series via the hardware interfaces is shown in FIG. 13C.

Figure 15:
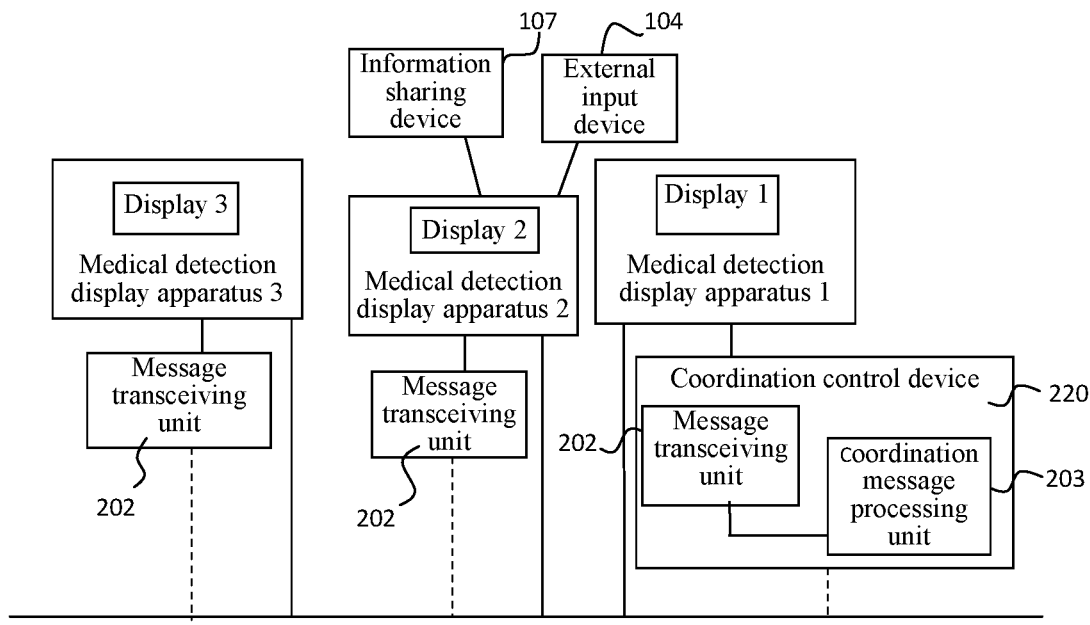

FIG. 15 provides one embodiment of another connection system architecture. In the present embodiment, the medical detection display apparatus 3 and the medical detection display apparatus 2 are respectively connected to a corresponding message transceiving unit 202. The message transceiving unit 202 herein may be an independent hardware device, and is connected to the medical detection display apparatus 100 via an interface matching an interface unit of the medical detection display apparatus 100, or may also be connected to the medical detection display apparatus 100 via a wireless network (such as Bluetooth or Wi-Fi). In addition, the medical detection display apparatus 1 is connected to a communication device 220. The communication device 220 is independent of the plurality of medical detection display apparatuses. The coordination message processing unit 203 and the message transceiving unit 202 connected thereto are provided on the communication device 220. As shown by the solid line portion in FIG. 15, the communication device 220 is connected to the medical detection display apparatus, so as to access a message communication channel formed by interconnecting the plurality of medical communication display devices. Alternatively, as shown by the dotted line portion in FIG. 15, the communication device 220 forms a message communication channel with independent hardware devices of the plurality of message transceiving units 202 by means of hardware interfaces or network connection. The message communication channel between the plurality of message transceiving units 202 is thus achieved. It may be seen that in one embodiment of the present disclosure, a message transceiving unit 202 is correspondingly connected to each of the medical detection display apparatuses 100, and the coordination message processing unit 203 and a message transceiving unit 202 connected thereto are provided on a communication device 220 independent of the plurality of medical detection display apparatuses, and access the message communication channel by being connected to one of the plurality of medical detection display apparatuses 100. Alternatively, the communication device 220 forms a message communication channel with the plurality of message transceiving units 202 that are not connected to the coordination message processing unit by means of hardware interfaces or network connection.

Figure 16:
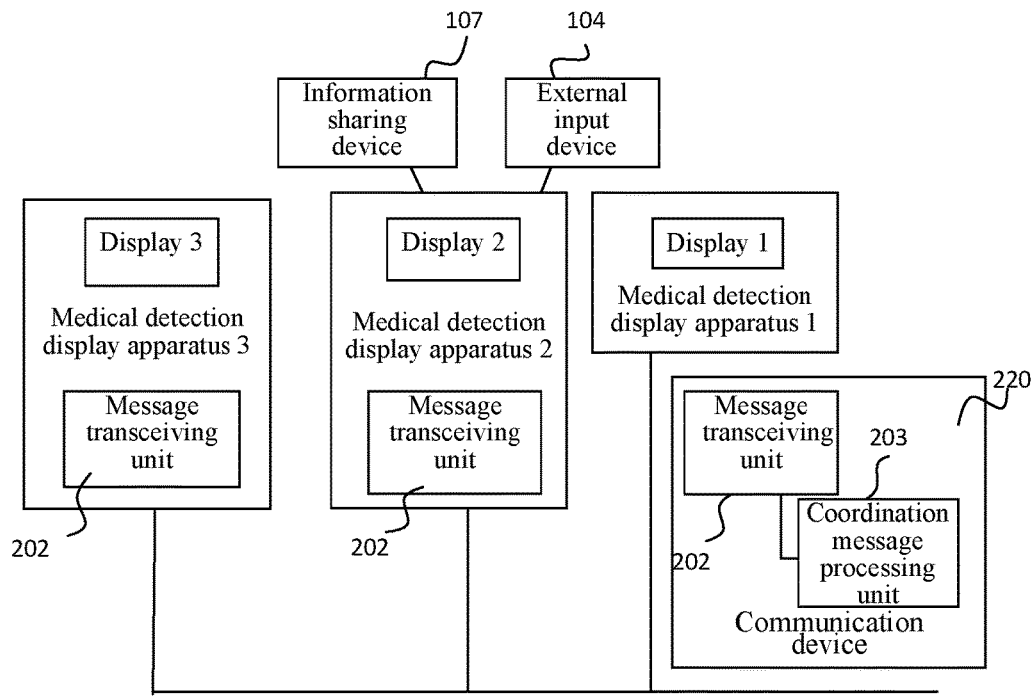

In addition, the message transceiving units 202 that are not connected to the communication device 220 in FIG. 15 can also be provided in the medical detection display apparatus 100, as shown in FIG. 16. In the embodiment provided by FIG. 16, a message transceiving unit 202 is provided in the medical detection display apparatus 3 and the medical detection display apparatus 2, respectively.

Based on the system connection relationship shown in FIGS. 15 and 16, the signal flow of a networked message communication channel may be as follows.

1. The message transceiving unit 202 provided corresponding to the medical detection display apparatus 2 forwards interaction information M1, which is acquired from the accessed external input device by the medical detection display apparatus 1 provided corresponding to the message transceiving unit itself, to a coordination message processing unit 203 on the communication device 220 connected to the medical communication display device 100.

2. The coordination message processing unit 203 on the communication device 220 receives the interaction information M1 from the message transceiving unit 202 connected thereto and converts the interaction information M1 into a display message M2. In this embodiment, it is assumed that the specified medical detection display apparatus corresponds to the medical detection display apparatus 3.

3. The message transceiving unit 202 connected to the coordination message processing unit 203 and located on the communication device 220 acquires, based on the identifier, transmission path information M3 corresponding to the medical detection display apparatus 3, and transmits a transmission message M4 carrying the display message M2 and the transmission path information M3 to the message transceiving unit 202 provided corresponding to the medical detection display apparatus 3 through a network.

4. The message transceiving unit 202 provided corresponding to the medical detection display apparatus 3 receives the transmission message M4 from the network, and outputs same to the display 3 corresponding to the medical detection display apparatus 3 to display the display message M2.

5. The message transceiving unit 202 on the medical detection display apparatus 2 forwards to the coordination message processing unit 203, which is located on the communication device 220 connected to the medical communication display device 1, shared information M5 acquired from the accessed information sharing device by the medical detection display apparatus 100 provided corresponding to the message transceiving unit.

6. The coordination message processing unit 203 on the communication device 220 further receives the shared information M5 from the message transceiving unit 202 connected thereto, and converts the shared information M5 into a presentation message M6.

7. The message transceiving unit 202 connected to the coordination message processing unit 203 and located on the communication device 220 transmits a transmission message M7 carrying the presentation message M6 and the transmission path information M3 to the message transceiving unit 202 provided corresponding to the medical detection display apparatus 3 through the network.

8. The message transceiving unit 202 provided corresponding to the medical detection display apparatus 3 receives the transmission message M7, and outputs same to the display 3 corresponding to the medical detection display apparatus 3 to display the presentation message M6.

The transmission path information M3 in this embodiment may be the network communication address of the message transceiving unit 202 connected to the coordination message processing unit 203 in the message communication channel, i.e., the network communication address corresponding to the medical detection display apparatus 3. The above-mentioned expression "provided corresponding to" includes being connected to the medical detection display apparatus and being provided on the medical detection display apparatus.

Based on the system connection relationship shown in FIGS. 15 and 16, the signal flow of a non-network message communication channel (that is, a communication channel formed by means of the direct serial connection via hardware interfaces) may be as follows.

1. The message transceiving unit 202 on the medical detection display apparatus 2 forwards to the coordination message processing unit 203, which is located on the communication device 220 connected to the medical communication display device 1, interaction information M1 acquired from the accessed external input device by the medical detection display apparatus 100 provided corresponding to the message transceiving unit itself. The forwarding mode is directly forwarding the information to the adjacent medical detection display apparatus 1, and receiving the information by the message transceiving unit 202 on the medical detection display apparatus 1 that conveys the information to the communication device 220.

2. The coordination message processing unit 203 on the communication device 220 receives the interaction information M1 from the message transceiving unit 202 connected thereto and converts the interaction information M1 into a display message M2. In this embodiment, it is assumed that the specified medical detection display apparatus corresponds to the medical detection display apparatus 3.

3. The message transceiving unit 202 on the medical detection display apparatus 220 conveys a transmission message M4 carrying the display message M2 and the transmission path information M3 to the medical detection display apparatus 1, forwards same to the message transceiving unit 202 provided on the adjacent medical detection display apparatus 2 on the message communication channel by means of an interface of the medical detection display apparatus 1, and then re-forwards same to the message transceiving unit 202 provided corresponding to the medical detection display apparatus 3 through the message transceiving unit 202 provided on the medical detection display apparatus 2.

4. The message transceiving unit 202 arranged corresponding to the medical detection display apparatus 3 receives the transmission message M4, and the display message M2 is output and displayed on the display 3 corresponding to the medical detection display apparatus 3.

5. The message transceiving unit 202 on the medical detection display apparatus 2 forwards to the coordination message processing unit 203, which is located on the communication device 220 connected to the medical communication display device 1, shared information M5 acquired from the accessed information sharing device by the medical detection display apparatus 100 provided corresponding to the message transceiving unit itself.

6. The coordination message processing unit 203 on the communication device 220 further receives the shared information M5 from the message transceiving unit 202 connected thereto, and converts the shared information M5 into a presentation message M6.

7. The message transceiving unit 202 on the medical detection display apparatus 220 conveys a transmission message M7 carrying the presentation message M6 and the transmission path information M3 to the medical detection display apparatus 1, forwards same to the message transceiving unit 202 provided on the adjacent medical detection display apparatus 2 on the message communication channel by means of an interface of the medical detection display apparatus 1, and then re-forwards same to the message transceiving unit 202 through the message transceiving unit 202 provided on the medical detection display apparatus 2.

8. The message transceiving unit 202 arranged corresponding to the medical detection display apparatus 3 receives the transmission message M7, and the presentation message M6 is output and displayed on the display 3 corresponding to the medical detection display apparatus 3.

The transmission path information M3 in this embodiment may be the information of a communication path of the message transceiving unit 202 connected to the coordination message processing unit 203 in the message communication channel, i.e., the network communication address corresponding to the medical detection display apparatus 1 to the medical detection display apparatus 3.

In the embodiment of FIG. 15 and FIG. 16 described above, a communication device 220 is used. The coordination message processing unit 203 and the message transceiving unit 202 connected thereto are provided on the communication device 220. The message transceiving unit 202 on the communication device 220 may be configured to execute the functions of the forwarding step S100, the receiving step S101, the searching step S400 and the sending step S500 in the method shown in FIG. 3 described above, and the coordination message processing unit 203 may be configured to execute the parsing step S200 and the converting step S300 in the method shown in FIG. 3 described above.

Figure 17:
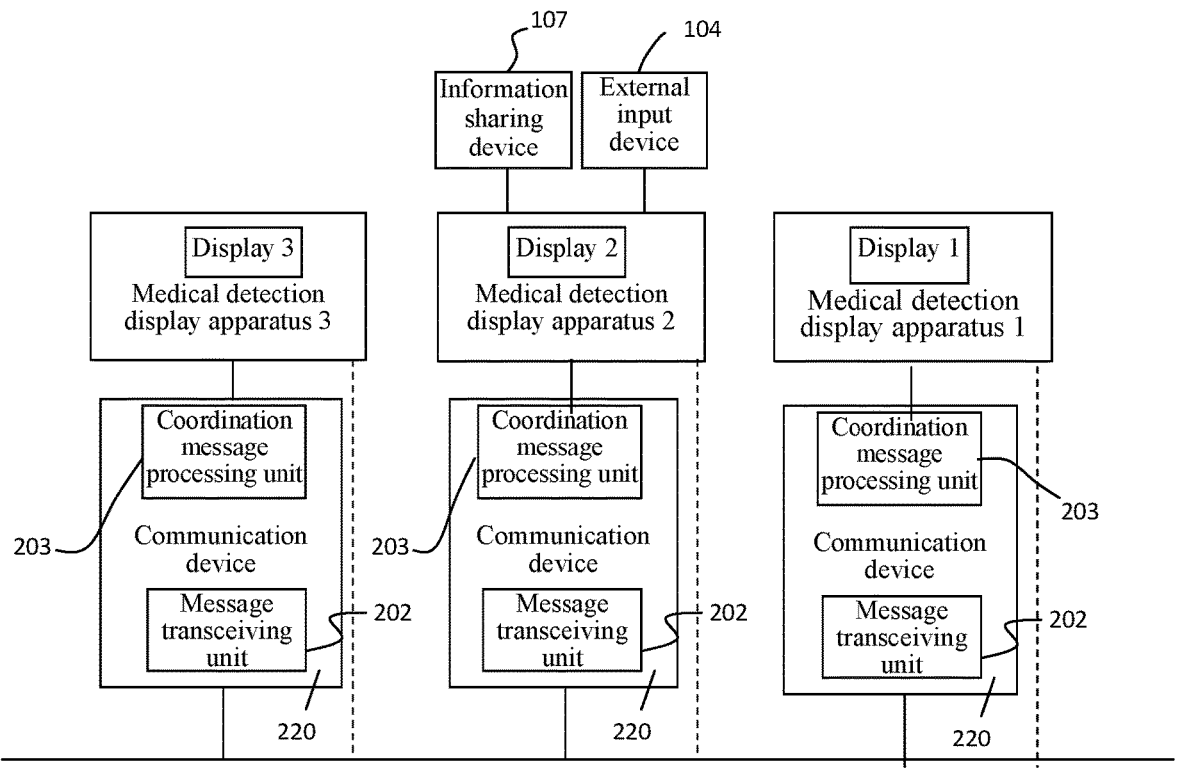

However, in the embodiment provided in FIG. 17, each of the medical detection display apparatuses is correspondingly connected to a communication device 220. This communication device 220 is similar to the communication device 220 in the embodiments shown in FIGS. 15 and 16. The difference lies in that it is necessary to set which communication device 220 is used as the central machine in the message communication channel according to the actual situation, and the parsing step S200 and the converting step S300 are executed by using the coordination message processing unit 203 provided thereon, so as to achieve the unified processing and parsing of messages in a certain period of time. As shown by the solid line in FIG. 17, the message communication channel may be obtained by connecting the plurality of communication devices 220. As shown by the dotted line in FIG. 17, the message communication channel may also be obtained by connecting the plurality of medical detection display apparatuses. Assume that the communication device 220 connected to the medical detection display apparatus 1 in FIG. 17 is used as the central machine, for the signal transmission process thereof, reference may be made to the foregoing description as shown in FIGS. 12B and 12C, and the description will not be repeated here. The difference lies in that there is a need for signal transfer between the communication device 220 and the medical detection display apparatus.

Figure 18:
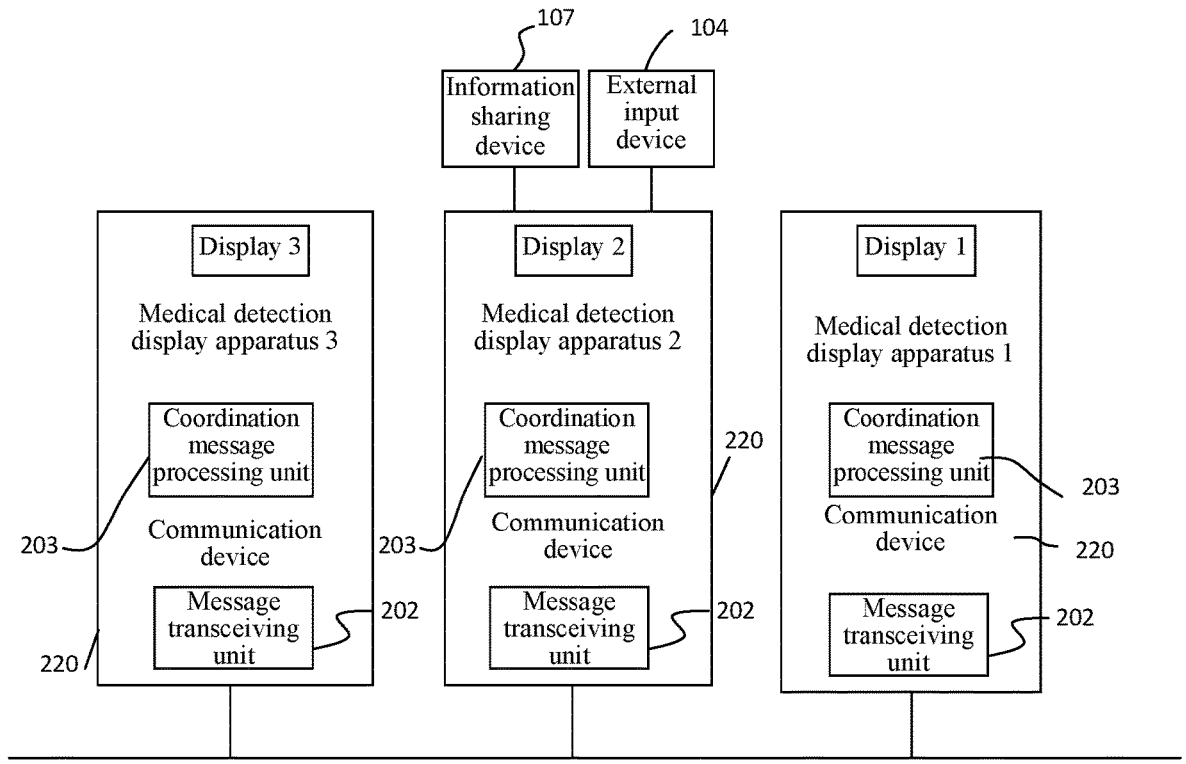

In the embodiment shown in FIG. 18, the difference from FIG. 11 lies in that a plurality of coordination message processing unit 203 and a plurality of message transceiving unit 202 are provided, and the plurality of message transceiving units 202 and the coordinated message processing units 203 are provided in pairs, and are both provided on each of the medical detection display apparatuses. The message transceiving unit 202 in this embodiment may be configured to execute the functions of the forwarding step S100, the receiving step S101, the searching step S400 and the sending step S500 in the method shown in FIG. 3 described above, and the coordination message processing unit 203 may be configured to execute the parsing step S200 and the converting step S300 in the method shown in FIG. 3 described above. Assume that the medical detection display apparatus 1 in FIG. 18 is used as the central machine, for the signal transmission process thereof, reference may be made to the foregoing description as shown in FIGS. 12B and 12C, and the description will not be repeated here.

For the embodiment with a plurality of coordination message processing units, one coordination message processing unit is activated in the same period of time for performing unified processing, forwarding, and allocation of messages, which is called a central machine. Regardless of any of the embodiments shown in FIGS. 12A to 18, when the coordination message processing unit is provided in one of the plurality of medical detection display apparatuses, and when one of the plurality of medical detection display apparatuses accesses the external input device, the coordination message processing unit may be activated to determine the identity of the central machine.

Alternatively, when a plurality of coordination message processing units are respectively provided on the plurality of medical detection display apparatuses (e.g., FIG. 18) or connected to the plurality of medical detection display apparatuses (e.g., FIG. 17), and when one of the plurality of medical detection display apparatuses accesses the external input device, the coordination message processing unit, which is provided corresponding to the medical detection display apparatus connected to the external input device, is activated and is marked as the central machine in the message communication channel, thereby determining the identity of the central machine in the message communication channel. As an example, as shown in FIG. 18, the coordination message processing unit provided on the medical detection display apparatus 2 is activated, and the medical detection display apparatus 2 is used as the central machine. As another example, as shown in FIG. 17, a coordination message processing unit 203 on the communication device 220 connected to the medical detection display apparatus 2 is activated and marked as the central machine in the message communication channel, and correspondingly, the medical detection display apparatus 2 or the communication device 220 connected to the medical detection display apparatus 2 is used as the central machine.

For the arrangement of a system with a plurality of coordination message processing units, in one embodiment of the present disclosure, one coordination message processing unit is activated in the same period of time and marked as the central machine in the message communication channel. Moreover, each of the coordination message processing units also needs to be configured to have the function of identifying its own identity and decide how to handle interaction information or shared information acquired by the message transceiving unit connected to the coordination message processing unit itself. As an example, the coordination message processing unit is further configured to determine whether the coordination message processing unit itself is a central machine, if so, parse the interaction information or the shared information acquired by the message transceiving unit connected to the coordination message processing unit itself, and if not, output a control instruction to make the message transceiving unit connected to the coordination message processing unit itself forward the interaction information or the shared information.

In the various embodiments described above, multiple connection relationships and arrangements of the message transceiving unit and the coordination message processing unit are provided. When the message transceiving unit is independent of the medical detection display apparatuses, it is possible to perform instruction configuration based on one or more processors in combination with an interface unit and a storage unit, so as to realize the corresponding functions. The communication device is further provided with a port matching a hardware interface of one of the plurality of medical detection display apparatuses 100, which is used to access the message communication channel by connecting one of the plurality medical detection display apparatuses, or by means of other wireless methods.

Of course, in addition to the above several configurations of the message transceiving unit 202 and the coordination message processing unit 203, other configurations may also be used, which will not be enumerated here. The plurality of the medical detection display apparatuses are connected to form a network to obtain a message communication channel, or the plurality of medical detection display apparatuses are connected in series via hardware interfaces to form a message communication channel, so that a message communication channel is provided between the plurality of message transceiving units 202.

In one embodiment of the present disclosure, each of the message transceiving units is configured to process the received forwarded message in one of the following ways, the forwarded message including the transmission message, the interaction information, or the shared information;

the message transceiving unit is configured to receive the forwarded message from the network, wherein the network communication address carried in the forwarded message is consistent with the network communication address of the message transceiving unit in the network, and the display information or the presentation message is output and displayed on the medical detection display apparatus corresponding to the message transceiving unit, or the interaction information or the shared information is sent to the coordination message processing unit, otherwise, the message transceiving unit discards the forwarded message which is received from the network with the carried network communication address being inconsistent with its own network communication address in the network; and the message transceiving unit is configured to receive the forwarded message from an adjacent message transceiving unit located on the message communication channel, if the communication path information carried by the forwarded message indicates that the message transceiving unit is a target node, the display information or the presentation message is output and displayed on the medical detection display apparatus corresponding to the message transceiving unit itself, or the interaction information or the shared information is transferred to the coordination message processing unit; otherwise, if the communication path information carried by the forwarded message indicates that the message transceiving unit is not a target node, the message transceiving unit forwards the forwarded message to the adjacent message transceiving unit located on the message communication channel, wherein the target node includes: the message transceiving unit corresponding to the specified medical detection display apparatus, or the message transceiving unit connected to the coordination message processing unit.

The above is generally used to configure the message transceiving unit to execute the reception functions in the receiving step and the delivery step shown in FIG. 3 described above. For details, reference may be made to the detailed description of the receiving step and the delivery step in the foregoing.

In one embodiment of the present disclosure, the coordination message processing unit is configured to execute the parsing step and the converting step shown in FIG. 3 described above, which may comprise: identifying cursor movement information in the interaction information; and then acquiring a specified medical detection display apparatus selected from the plurality of medical detection display apparatuses by the user according to the cursor movement information, and seeking the identifier corresponding to the specified medical detection display apparatus. In addition, the coordination message processing unit is further configured to determine, according to pre-stored display installation position relationships of the plurality of medical detection display apparatuses and based on the cursor movement information, the correspondence relationship between the motion of a cursor and the display installation position relationship, so as to identify the specified medical detection display apparatus from the plurality of medical detection display apparatuses. For the way in which how the coordination message processing unit acquires the specified medical detection display apparatus selected from the plurality of medical detection display apparatuses by the user according to the cursor movement information, reference may be made to the related explanation about the parsing step in the foregoing.

In one embodiment of the present disclosure, one of the plurality of medical detection display apparatuses is configured to display the display installation position relationships of the plurality of medical detection display apparatuses, and/or the display requirements corresponding to each of the medical detection display apparatuses, acquire a user's configuration instruction data via the external input device, and adjust the display installation position relationships and/or the display requirements corresponding to each of the medical detection display apparatuses according to the configuration instruction.

In one embodiment of the present disclosure, when the message transceiving units respectively provided corresponding to the plurality of medical detection display apparatuses receive that the external input device or the information sharing device accesses the medical detection display apparatus arranged corresponding to the message transceiving unit itself, the medical detection display apparatus arranged corresponding to the message transceiving unit itself outputs and displays a prompt box for prompting the user to select whether to activate the coordination message processing unit.

Based on the related description of the communication device 200 provided in the foregoing, in combination with the various embodiments shown in FIGS. 15, 16, 17 and 18, a new communication device is further provided in one embodiment of the present disclosure. The communication device further includes:

a communication unit further configured to receive interaction information acquired from an external input device accessing the medical detection display apparatus connected to itself (referring to the communication device); and/or, a communication unit further configured to receive shared information acquired from an external input device accessing the medical detection display apparatus connected to itself.

In addition, in one embodiment of the present disclosure, on the communication device, the processing unit is further configured to determine whether the communication device is the central device in the message communication channel; if yes, the received interaction information or shared information is parsed; otherwise, the communication unit forwards the acquired interaction information or shared information to the message communication channel.

Figure 19:
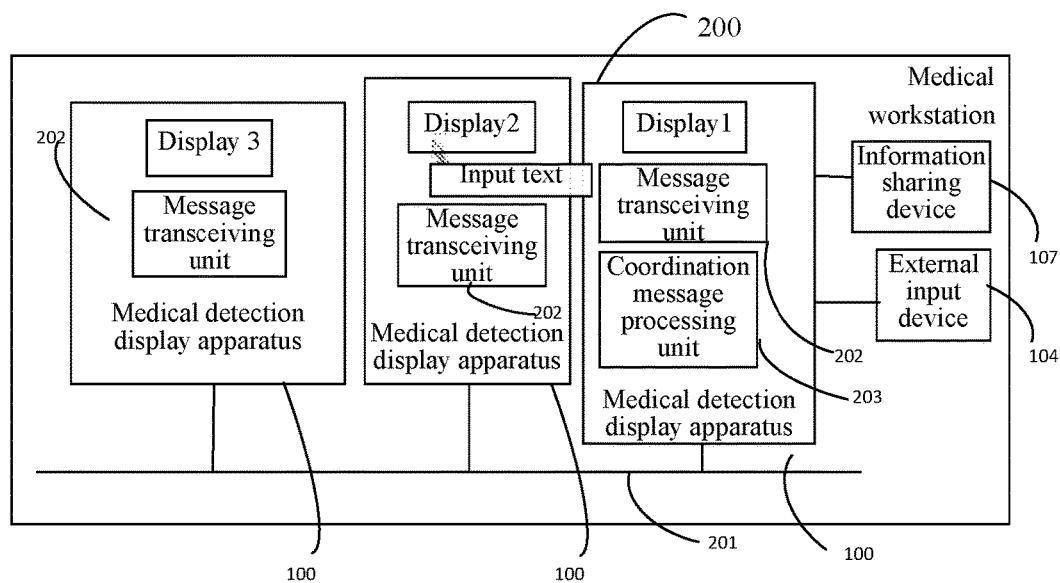
FIG. 19 is a schematic structural diagram of a medical workstation in one embodiment of the present disclosure.

Based on the various embodiments described above, as shown in FIGS. 12A to 18, a medical workstation is further provided in one of the embodiments of the present disclosure, and reference may be made to the medical workstation shown in FIG. 19 and combined with the systematic structure shown in FIG. 12A. The medical workstation includes a plurality of medical detection display apparatuses 100, an external input device 104 connected to one of the plurality of medical detection display apparatuses, and a system for controlling coordination between medical devices as described in any one of the above embodiments. The system includes a plurality of message transceiving units 202 and a coordination message processing unit 203, wherein the plurality of medical detection display apparatuses are connected to each other to form a message communication channel between the plurality of message transceiving units; and each of the medical detection display apparatuses is provided with the corresponding message transceiving unit.

In addition, the medical workstation includes: an information sharing device 107 for being connected to one of the plurality of medical detection display apparatuses 100. The medical detection display apparatus 100 connected to the information sharing device is configured to acquire shared information from the information sharing device 107, and forward the shared information to the message transceiving unit connected to the coordination message processing unit through the message transceiving unit provided corresponding to the medical detection display apparatus itself; the coordination message processing unit is configured to receive the shared information from the message transceiving unit connected thereto, and convert the received shared information into a presentation message matching the specified medical detection display apparatus; and the coordination message processing unit connected to the message transceiving unit is configured to transmit the transmission message carrying the presentation message and the transmission path information to the message transceiving unit provided corresponding to the specified medical detection display apparatus via the message communication channel, so that the message transceiving unit receives the transmission message and the presentation message is output and displayed on the specified medical detection display apparatus.

Figure 20:
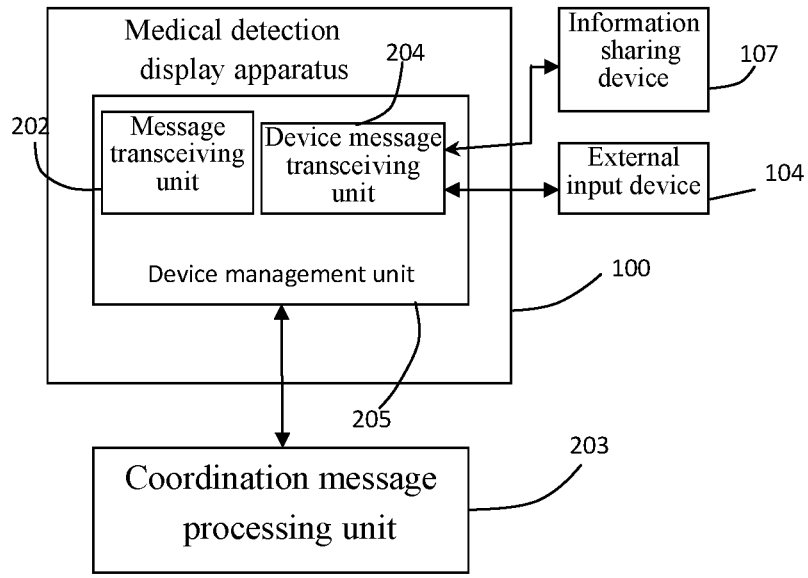
FIG. 20 is a schematic structural diagram of an association between information of a medical detection display apparatus and a coordination message processing unit in one embodiment of the present disclosure.

In the embodiment shown in FIG. 20, a device message transceiving unit 204 connected to the external input device or the information sharing device is further provided on each of the medical detection display apparatuses 100, and by acquiring the interaction information or the shared information input from the external input device or the information sharing device by the device message transceiving units 204, the information is synchronized between the message transceiving units 202 and the device message transceiving units.

According to the coordinated operation communication device and system in the various embodiments described above, the aforementioned coordination message processing unit 203 is transformed to form a message processing client, and the message processing client may be directly loaded and run on the medical detection display apparatus 100, or the formed message processing client is stored on the external input device and/or the information sharing device 107. When the external input device and/or the information sharing device 107 access the medical detection display apparatus 100, the corresponding message processing client runs on the medical detection display apparatus 100, so as to implement the coordinated operation system and the communication device in the various embodiments described above. Similarly, it may also be possible to provide each external device (such as the external input device 104 and/or the information sharing device 107) with the device message transceiving unit and the message transceiving unit. The two-way transmission control is performed between the message transceiving unit and the message processing client. This control communication device and message flow is equivalent to actual external devices. From the point of view of a certain medical detection display apparatus 100, the message sources are not distinguished whether from an actual device port corresponding to the message transceiving unit or from a virtual device port corresponding to the message transceiving unit.

In the various embodiments described above, a message processing client runs by default on the medical detection display apparatus of any connected device, and different devices (a display 1, a display 2, a display 3, etc.) to be controlled are virtualized on the message processing client. That is to say, the coordination message processing unit generates virtual device ports, which correspond to the plurality of medical detection display apparatuses in the network, on the running medical detection display apparatuses for receiving the information conveyed from the message transceiving unit on the medical detection display apparatus in the network.

All the external input devices and/or information sharing devices 107 accessing the machine running the message processing client take over all the external input devices and/or information sharing devices connected to such a device through in a networked or non-networked manner by means of the message processing client. 107. The message processing client internally performs unified processing on the messages, and the processed messages are delivered to the final actual device end through the network or a transmission channel such as a serial port according to the requirements of management of the virtual device.

Those skilled in the art could, from the above description about the embodiments, clearly understand that the methods of the various embodiments describe above may be implemented by means of software combined with a necessary general-purpose general hardware platform, and of course, or may be implemented by means of the hardware, but in many cases the former is better implementation. Based on this understanding, the technical solutions of the present disclosure substantively, or a part thereof making a contribution to the prior art, may be reflected in the form of computer software product, which is stored in a non-volatile computer-readable storage medium such as a ROM/RAM, a magnetic disk, optical disk and a server cloud space, and include several instructions to enable a terminal device, which may be a mobile phone, a computer, a server, or a network device, etc., to implement the systematic structures, devices and methods of the embodiments of the present disclosure.

The above-mentioned examples merely represent several embodiments, giving specifics and details thereof, but should not be understood as limiting the scope of the present patent of disclosure thereby. It should be noted that a person of ordinary skill in the art could also make some alterations and improvements without departing from the spirit of the present disclosure and these would all fall within the scope of protection of the present disclosure. Therefore, the scope of protection of the present patent of disclosure shall be in accordance with the appended claims.

The invention claimed is:

1. A system for controlling coordination between a plurality of medical detection display apparatuses, wherein each of the plurality of medical detection display apparatuses comprises a respective external input device and a respective display device, wherein the system comprises:
    a plurality of message transceiving units respectively corresponding to the plurality of medical detection display apparatuses; and one or more message communication channels, each of the message communication channels is provided between two of the plurality of message transceiving units; and
    a plurality of coordination message processing units, each of which is respectively connected to one of the plurality of message transceiving units, wherein each of the plurality of coordination message processing units receives interaction information from the message transceiving unit connected thereto, parses the interaction information to obtain an identifier corresponding to a medical detection display apparatus specified from the plurality of medical detection display apparatuses, and converts, according to a display requirement corresponding to the identifier, the interaction information into a corresponding display message for display on the specified medical detection display apparatus;
    wherein each of the plurality of message transceiving units is configured to acquire interaction information from any one of the respective external input devices of the plurality of medical detection display apparatuses and forward the interaction information to the coordination message processing unit connected to said message transceiving unit;
    wherein each of the plurality of message transceiving units is further configured to acquire, based on the identifier, information about a transmission path of the specified medical detection display apparatus via the message communication channel between said message transceiving unit and the message transceiving unit corresponding to the specified medical detection display apparatus, and transmit a transmission message carrying the display message and the transmission path information to the message transceiving unit corresponding to the specified medical detection display apparatus via said message communication channel, and output the display message to the respective display device of the specified medical detection display apparatus, wherein any one of the plurality of medical detection display apparatuses is controllable by another one of the plurality of medical detection display apparatuses;
    wherein each of the plurality of coordination message processing units is capable of functioning as a central machine in the message communication channels; and
    wherein each of the plurality of coordination message processing units is configured to: determine whether the coordination message processing unit itself is currently a central machine after receiving the interaction information, parse the interaction information when determining that the coordination message processing unit itself is currently a central machine, and output a control instruction, when determining that the coordination message processing unit itself is currently not a central machine, to make the message transceiving unit that is connected to said coordination message processing unit forward the interaction information to another one of the plurality of medical detection display apparatuses currently functioned as a central machine.

2. The system of claim 1, wherein each of the plurality of message transceiving units is further configured to forward shared information, which is acquired by the medical detection display apparatus corresponding to said message transceiving unit from an accessed information sharing device, to the coordination message processing unit that is connected to said message transceiving unit; each of the plurality of coordination message processing units is further configured to receive the shared information from the message transceiving unit that is connected thereto, and convert the shared information into a presentation message matching the specified medical detection display apparatus; and wherein each of the plurality of message transceiving units connected to each of the plurality of coordination message processing units is configured to transmit a transmission message carrying the presentation message and the transmission path information to the specified message transceiving unit provided corresponding to the specified medical detection display apparatus via the message communication channel, and output the presentation message via the specified medical detection display apparatus.

3. The system of claim 1, wherein each of the plurality of message transceiving units is provided in each of the plurality of medical detection display apparatuses, or outside the medical detection display apparatus.

4. The system of claim 1, wherein access of the each of the plurality of coordination message processing units to the message communication channel is implemented in one of the following ways:

each of the plurality of coordination message processing units is at least provided in one of the plurality of medical detection display apparatuses; and each of the plurality of coordination message processing units and the message transceiving unit that is connected to said coordination message processing unit are provided on a communication device located outside the plurality of medical detection display apparatuses, and the communication device is connected to the plurality of medical detection display apparatuses to form a network to access the message communication channel, or the communication device is connected to one of the plurality of medical detection display apparatuses via a hardware interface to access the message communication channel.

5. The system of claim 2, wherein the transmission path information comprises: a corresponding network communication address of each of the message transceiving units in the network, or information about a communication path between each of the message transceiving units.

6. The system of claim 5, wherein the system further comprises: a first storage unit configured to store an association relationship between the identifier corresponding to each of the medical detection display apparatuses and the network communication address; or to store a correspondence relationship between the identifier and the communication path information.

7. The system of claim 5, wherein each of the plurality of message transceiving units is configured to embed the network communication address in the network into the interaction information or the shared information, and send same to the network to forward the interaction information or the shared information to each of the plurality of coordination message processing units; or each of the plurality of message transceiving units is configured to embed the communication path information into the interaction information or the shared information, and forward same to an adjacent message transceiving unit located on the message communication channel to forward the interaction information or the shared information to the coordination message processing unit that is connected to said message transceiving unit, wherein the communication path information is information about a communication path between an adjacent two of the plurality of message transceiving units.

8. The system of claim 5, wherein each of the message transceiving units is configured to process the received forwarded message in one of the following ways, the forwarded message comprising the transmission message, the interaction information, or the shared information:

each of the plurality of message transceiving units is configured to receive the forwarded message from the network, wherein the network communication address carried in the forwarded message is consistent with the network communication address of each of the plurality of message transceiving units in the network, and the display information or the presentation message is output and displayed on one of the medical detection display apparatuses corresponding to the message transceiving unit that is connected to said medical detection display apparatus, or the interaction information or the shared information is sent to the coordination message processing unit that is connected to said message transceiving unit; and each of the plurality of message transceiving units is configured to receive the forwarded message from an adjacent message transceiving unit located on the message communication channel, if the communication path information carried by the forwarded message indicates that said message transceiving unit is a target node, the display information or the presentation message is output and displayed on one of the medical detection display apparatuses corresponding to the message transceiving unit that is connected to said medical detection display apparatus, or the interaction information or the shared information is transferred to the coordination message processing unit that is connected to said message transceiving unit, and if the communication path information carried by the forwarded message indicates that said message transceiving unit is not a target node, this message transceiving unit forwards the forwarded message to the adjacent message transceiving unit located on the message communication channel, wherein the target node comprises: each of the plurality of message transceiving units corresponding to the specified medical detection display apparatus.

9. The system of claim 8, wherein each of the plurality of message transceiving units is configured to determine whether the communication path information carried in the forwarded message indicates that said message transceiving unit is a target node in at least one of the following ways:

determining whether a number of times of forwarding required in the process of reaching the target node and included in the communication path information is zero, and if the number of times of forwarding is zero, indicating that the said message transceiving unit is a target node, otherwise said message transceiving unit is a non-target node, and decrementing the number of times of forwarding and embedding same to the forwarded message forwarded to the adjacent medical detection display apparatus; and determining whether a number corresponding to the target node and included in the communication path information is a number corresponding to each of the plurality of message transceiving units itself, and if so, indicating that said message transceiving unit is a target node, otherwise the message transceiving unit itself is a non-target node.

10. The system of claim 1, wherein each of the plurality of coordination message processing units is configured to identify cursor movement information in the interaction information, acquire a specified medical detection display apparatus selected from the plurality of medical detection display apparatuses by a user according to the cursor movement information, and seek the identifier corresponding to the specified medical detection display apparatus.

11. The system of claim 10, wherein each of the plurality of coordination message processing units is further configured to determine, according to pre-stored display installation position relationships of the plurality of medical detection display apparatuses and based on the cursor movement information, a correspondence relationship between motion of a cursor and the display installation position relationship, so as to identify the specified medical detection display apparatus from the plurality of medical detection display apparatuses.

12. The system of claim 11, wherein each of the plurality of coordination message processing units is further configured to acquire the specified medical detection display apparatus selected from the plurality of medical detection display apparatuses by the user according to the cursor movement information in one of the following ways:

when cursor movement speed and/or cursor movement displacement in the cursor movement information exceed(s) a predetermined threshold(s), a medical detection display apparatus installed at a position adjacent to the medical detection display apparatus where the cursor is located before movement is selected in a cursor movement direction in the cursor movement information as the specified medical detection display apparatus; and when the cursor is controlled to move to a boundary of a current display interface, the cursor movement information still indicates that the cursor is to move in a direction crossing the boundary, a medical detection display apparatus installed at a position adjacent to the medical detection display apparatus where the cursor is located before movement is selected in the cursor movement direction as the specified medical detection display apparatus.

13. The system of claim 12, wherein each of the plurality of coordination message processing units is further configured to identify the specified medical detection display apparatus from the plurality of medical detection display apparatuses in one of the following ways:

a virtual operation coordinate map corresponding, on a one-to-one basis, to the display installation position relationship is formed based on an operation attribute of an accessed external input device, each of the medical detection display apparatuses corresponds to a coordinate area, which coordinate area a motion result of the cursor is located in on the virtual operation coordinate map is sought according to the cursor movement information, and according to the sought coordinate area, the medical detection display apparatus corresponding to the coordinate area is selected from the plurality of medical detection display apparatuses as the specified medical detection display apparatus; and a virtual position coordinate map corresponding to the display installation position relationship is formed, each of the medical detection display apparatuses sets a motion position area in the virtual position coordinate map, and it is determined whether the cursor movement displacement in the cursor movement information exceeds the motion position area, if yes, reference is made to the virtual position coordinate map, in a cursor movement direction, the medical detection display apparatus corresponding to a motion position range to which the cursor movement displacement spans is selected as the specified medical detection display apparatus, or the medical detection display apparatus positioned adjacent to the medical detection display apparatus where the cursor is displayed before being moved as the specified medical detection display apparatus.

14. The system of claim 13, wherein when the cursor movement speed and/or cursor movement displacement do(es) not exceed the predetermined threshold(s), or when the cursor movement displacement does not exceed the motion position area, the medical detection display apparatus where the cursor is displayed before being moved is used as the specified medical detection display apparatus.

15. The system of claim 13, wherein one of the plurality of medical detection display apparatuses is configured to display the display installation position relationships of the plurality of medical detection display apparatuses, and/or the display requirements corresponding to each of the medical detection display apparatuses, acquire a user's configuration instruction data via the external input device, and adjust the display installation position relationships and/or the display requirements corresponding to each of the medical detection display apparatuses according to the configuration instruction.

16. The system of claim 14, wherein the medical detection display apparatus where the cursor is displayed before being moved comprises: the medical detection display apparatus connected to the external input device.

17. The system of claim 1, wherein, in the system, when each of the plurality of coordination message processing units is provided in each of the plurality of medical detection display apparatuses, and when one of the plurality of medical detection display apparatuses accesses the external input device, the coordination message processing unit that is connected to said medical detection display apparatus is activated; or when the plurality of coordination message processing units are respectively provided on the plurality of medical detection display apparatuses or connected to the plurality of medical detection display apparatuses, and when one of the plurality of medical detection display apparatuses accesses the external input device, the coordination message processing unit that is provided corresponding to the medical detection display apparatus connected to the external input device, is activated.

18. The system of claim 2, wherein each of the plurality of coordination message processing units is further configured to: parse the shared information acquired by the message transceiving unit that is connected to said coordination message processing unit when one of the coordination message processing unit is determined to be a central machine, parse the interaction information or the shared information acquired by the message transceiving unit that is connected to said coordination message processing unit, and output a control instruction to make the message transceiving unit that is connected to said coordination message processing unit forward the shared information when one of the coordination message processing unit is determined not to be a central machine.

19. A system for controlling coordination between a plurality of medical detection display apparatuses, wherein each of the plurality of medical detection display apparatuses comprises a respective external input device and a respective display device, wherein the system comprises:
a plurality of message transceiving units respectively corresponding to the plurality of medical detection display apparatuses; and a coordination message processing unit connected to one of the plurality of message transceiving units; and one or more message communication channels being provided between any one of the plurality of message transceiving units and another one connected to said coordination message processing unit; and
wherein the message transceiving units, which are respectively provided corresponding to the plurality of medical detection display apparatuses, are configured to acquire interaction information from a selected one of the respective external input devices of the plurality of medical detection display apparatuses and forward the interaction information to the coordination message processing unit;
wherein the coordination message processing unit is configured to receive the interaction information from the message transceiving unit connected thereto, parse the interaction information to obtain an identifier corresponding to a medical detection display apparatus specified by a user, and convert, according to a display requirement corresponding to the identifier, the interaction information into a corresponding display message for display on the specified medical detection display apparatus; and
wherein the message transceiving unit connected to the coordination message processing unit is configured to acquire, based on the identifier, information about a transmission path of the specified medical detection display apparatus via the message communication channel between said message transceiving unit and the message transceiving unit corresponding to the specified medical detection display apparatus, and transmit a transmission message carrying the display message and the transmission path information to the message transceiving unit provided corresponding to the specified medical detection display apparatus via the message communication channel, and output the display message to the specified medical detection display apparatus to the respective display device of the specified medical detection display apparatus, wherein any one of the plurality of medical detection display apparatuses is controllable by another one of the plurality of medical detection display apparatuses;
wherein each of the plurality of coordination message processing units is capable of functioning as a central machine in the message communication channels; and
wherein each of the plurality of coordination message processing units is configured to: determine whether the coordination message processing unit itself is currently a central machine after receiving the interaction information, parse the interaction information when determining that the coordination message processing unit itself is currently a central machine, and output a control instruction, when determining that the coordination message processing unit itself is currently not a central machine, to make the message transceiving unit that is connected to said coordination message processing unit forward the interaction information to another one of the plurality of medical detection display apparatuses currently functioned as a central machine.

20. The system of claim 19, wherein each of the message transceiving units is further configured to forward shared information, which is acquired by the medical detection display apparatus provided corresponding to the said message transceiving unit from an accessed information sharing device, to the coordination message processing unit; the coordination message processing unit is further configured to receive the shared information from the message transceiving unit connected thereto, and convert the shared information into a presentation message matching the specified medical detection display apparatus; and
wherein the message transceiving unit connected to the coordination message processing unit is configured to transmit a transmission message carrying the presentation message and the transmission path information to the message transceiving unit provided corresponding to the specified medical detection display apparatus via the message communication channel, and output the presentation message via the specified medical detection display apparatus.

21. The system of claim 20, wherein the transmission path information comprises: a corresponding network communication address of each of the message transceiving units in the network, or information about a communication path between each of the message transceiving units and the message transceiving unit connected to the coordination message processing unit.

22. The system of claim 21, wherein the message transceiving unit is configured to embed the network communication address of the message transceiving unit connected to the coordination message processing unit in the network into the interaction information or the shared information, and send same to the network to forward the interaction information or the shared information to the coordination message processing unit; or
the message transceiving unit is configured to embed the communication path information into the interaction information or the shared information, and forward same to an adjacent message transceiving unit located on the message communication channel to forward the interaction information or the shared information to the coordination message processing unit, wherein the communication path information is information about a communication path between this message transceiving unit and the message transceiving unit connected to the coordination message processing unit.

23. The system of claim 21, wherein each of the message transceiving units is configured to process the received forwarded message in one of the following ways, the forwarded message comprising the transmission message, the interaction information, or the shared information:

the message transceiving unit is configured to receive the forwarded message from the network, wherein the network communication address carried in the forwarded message is consistent with the network communication address of the message transceiving unit in the network, and the display information or the presentation message is output and displayed on the medical detection display apparatus corresponding to the message transceiving unit, or the interaction information or the shared information is sent to the coordination message processing unit; and the message transceiving unit is configured to receive the forwarded message from an adjacent message transceiving unit located on the message communication channel, if the communication path information carried by the forwarded message indicates that the message transceiving unit is a target node, the display information or the presentation message is output and displayed on the medical detection display apparatus corresponding to the message transceiving unit, or the interaction information or the shared information is transferred to the coordination message processing unit, and if the communication path information carried by the forwarded message indicates that the message transceiving unit is not a target node, the message transceiving unit forwards the forwarded message to the adjacent message transceiving unit located on the message communication channel, wherein the target node comprises: the message transceiving unit corresponding to the specified medical detection display apparatus, or the message transceiving unit connected to the coordination message processing unit.

24. The system of claim 1, wherein the transmission path information further comprises at least one of:

a sequence of all the plurality of medical detection display apparatuses that have passed during the process of reaching a target node, wherein the target node is an object to which the message was finally transmitted; or corresponding numbers of the plurality of medical detection display apparatuses that have passed during the process of reaching a target node in the transmission path information, wherein the target node is an object to which the message was finally transmitted; or a corresponding number of a target node in the transmission path information, wherein the target node is an object to which the message was finally transmitted; or a number of times of forwarding required to reach a target node, wherein the target node is an object to which the message was finally transmitted; or a corresponding number of a target node and a number of times of forwarding required to reach the target node, wherein the target node is an object to which the message was finally transmitted.

25. The system of claim 19, wherein the transmission path information further comprises at least one of:

a sequence of all the plurality of medical detection display apparatuses that have passed during the process of reaching a target node, wherein the target node is an object to which the message was finally transmitted; or corresponding numbers of the plurality of medical detection display apparatuses that have passed during the process of reaching a target node in the transmission path information, wherein the target node is an object to which the message was finally transmitted; or a corresponding number of a target node in the transmission path information, wherein the target node is an object to which the message was finally transmitted; or a number of times of forwarding required to reach a target node, wherein the target node is an object to which the message was finally transmitted; or a corresponding number of a target node and a number of times of forwarding required to reach the target node, wherein the target node is an object to which the message was finally transmitted.

* * * * *